(12) United States Patent
Smith et al.

(10) Patent No.: US 10,188,520 B2
(45) Date of Patent: *Jan. 29, 2019

(54) MODULAR LATERAL HIP AUGMENTS

(71) Applicant: Biomet Manufacturing, LLC, Warsaw, IN (US)

(72) Inventors: Aaron P. Smith, Warsaw, IN (US); Tyler D. Witt, Warsaw, IN (US); Hugh Apthorp, East Sussex (GB); Keith R. Berend, Columbus, OH (US); Andrew Freiberg, Weston, MA (US); John Barrington, Pano, TX (US); David R. Brown, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 68 days.

This patent is subject to a terminal disclaimer.

(21) Appl. No.: 15/338,957

(22) Filed: Oct. 31, 2016

(65) Prior Publication Data

US 2017/0042685 A1 Feb. 16, 2017

Related U.S. Application Data

(60) Continuation of application No. 14/563,118, filed on Dec. 8, 2014, now Pat. No. 9,510,950, which is a
(Continued)

(51) Int. Cl.
*A61F 2/32* (2006.01)
*A61F 2/36* (2006.01)
*A61F 2/30* (2006.01)

(52) U.S. Cl.
CPC ........ *A61F 2/3672* (2013.01); *A61F 2/30734* (2013.01); *A61F 2/30739* (2013.01);
(Continued)

(58) Field of Classification Search
CPC .......... A61F 2/30739; A61F 2002/3627; A61F 2/367; A61F 2/3601; A61F 2/30734; A61F 2002/30736; A61F 2002/368
See application file for complete search history.

(56) References Cited

U.S. PATENT DOCUMENTS 1,714,684 A 5/1929 Malcolm
2,231,864 A 2/1941 Abel
(Continued)

FOREIGN PATENT DOCUMENTS

DE 4320086 A1 12/1994
DE 29516473 U1 12/1995
(Continued)

OTHER PUBLICATIONS

"U.S. Appl. No. 12/718,230, Non Final Office Action dated Nov. 7, 2012", 16 pgs.
(Continued)

*Primary Examiner* — David H Willse
*Assistant Examiner* — Javier Blanco
(74) *Attorney, Agent, or Firm* — Schwegman Lundberg & Woessner, P.A.

(57) ABSTRACT

An implant for a hip can include a lateral augment adapted to be coupled to a lateral side of a femoral body implant. The lateral augment can include a body portion having a first surface, a second surface opposite the first surface, and a protrusion extending from the second surface. The protrusion can have a shape adapted to mate with a complementary shaped recess formed in the lateral side of the femoral body implant. An aperture can be positioned in the body portion and extend through the protrusion. A fastener can be received through the aperture and adapted to be threadably secured to the lateral bore. The fastener can be configured to have a length sufficient to pass through a portion of a greater
(Continued)

trochanter for securing the portion of the greater trochanter and the lateral augment to the femoral body implant.

14 Claims, 23 Drawing Sheets

Related U.S. Application Data division of application No. 13/913,858, filed on Jun. 10, 2013, now Pat. No. 8,906,109, which is a division of application No. 12/718,230, filed on Mar. 5, 2010, now Pat. No. 8,460,393.

(52) U.S. Cl.
CPC .............. *A61F 2/32* (2013.01); *A61F 2/3601* (2013.01); *A61F 2/367* (2013.01); *A61F 2002/368* (2013.01); *A61F 2002/3627* (2013.01); *A61F 2002/3674* (2013.01); *A61F 2002/3686* (2013.01); *A61F 2310/00011* (2013.01)

(56) References Cited

U.S. PATENT DOCUMENTS

| | | | |
|---|---|---|---|
| 2,511,051 A * | 6/1950 | Dzus | A61B 17/683 411/338 |
| 3,489,143 A * | 1/1970 | Halloran | A61B 17/746 606/282 |
| 3,815,599 A | 6/1974 | Deyerle | |
| 4,012,796 A | 3/1977 | Weisman | |
| 4,306,550 A | 12/1981 | Forte | |
| 4,535,487 A | 8/1985 | Esper et al. | |
| 4,549,319 A | 10/1985 | Meyer | |
| 4,552,136 A | 11/1985 | Kenna | |
| 4,601,289 A | 7/1986 | Chiarizzio et al. | |
| 4,718,915 A | 1/1988 | Epinette | |
| 4,728,333 A | 3/1988 | Masse et al. | |
| 4,770,660 A | 9/1988 | Averill | |
| 4,790,852 A | 12/1988 | Noiles | |
| 4,842,606 A | 6/1989 | Kranz et al. | |
| 4,883,492 A | 11/1989 | Frey et al. | |
| 4,904,269 A | 2/1990 | Elloy et al. | |
| 4,959,066 A | 9/1990 | Dunn et al. | |
| 5,041,118 A | 8/1991 | Wasilewski | |
| 5,047,035 A | 9/1991 | Mikhail et al. | |
| 5,061,271 A | 10/1991 | Van Zile | |
| 5,080,685 A | 1/1992 | Bolesky et al. | |
| 5,089,004 A | 2/1992 | Averill et al. | |
| 5,092,900 A | 3/1992 | Marchetti et al. | |
| 5,122,146 A | 6/1992 | Chapman et al. | |
| 5,201,769 A | 4/1993 | Schutzer | |
| 5,211,666 A | 5/1993 | Fetto | |
| 5,376,124 A | 12/1994 | Gustke et al. | |
| 5,409,492 A | 4/1995 | Jones et al. | |
| 5,468,243 A | 11/1995 | Halpern | |
| 5,489,284 A | 2/1996 | James et al. | |
| 5,562,666 A | 10/1996 | Brumfield | |
| 5,571,111 A | 11/1996 | Aboczky | |
| 5,578,037 A | 11/1996 | Sanders et al. | |
| 5,601,564 A | 2/1997 | Gustilo et al. | |
| 5,607,431 A | 3/1997 | Dudasik et al. | |
| 5,624,445 A | 4/1997 | Burke | |
| 5,632,747 A | 5/1997 | Scarborough et al. | |
| 5,645,549 A | 7/1997 | Boyd et al. | |
| 5,649,930 A | 7/1997 | Kertzner | |
| 5,665,090 A | 9/1997 | Rockwood et al. | |
| 5,683,470 A | 11/1997 | Johnson et al. | |
| 5,690,636 A | 11/1997 | Wildgoose | |
| 5,699,915 A | 12/1997 | Berger et al. | |
| 5,704,940 A | 1/1998 | Garosi | |
| 5,766,261 A | 6/1998 | Neal et al. | |
| 5,766,262 A | 6/1998 | Mikhail | |
| 5,776,194 A | 7/1998 | Mikol et al. | |
| 5,788,701 A | 8/1998 | Mccue | |
| 5,849,015 A | 12/1998 | Haywood et al. | |
| 5,860,969 A | 1/1999 | White et al. | |
| 5,860,982 A | 1/1999 | Ro et al. | |
| 5,908,423 A | 6/1999 | Kashuba et al. | |
| 5,913,860 A | 6/1999 | Scholl | |
| 5,976,145 A | 11/1999 | Kennefick, III | |
| 5,989,261 A | 11/1999 | Walker et al. | |
| 6,022,357 A | 2/2000 | Reu et al. | |
| 6,027,505 A | 2/2000 | Peter et al. | |
| 6,033,405 A | 3/2000 | Winslow et al. | |
| 6,066,173 A | 5/2000 | Mckernan et al. | |
| 6,110,179 A | 8/2000 | Flivik et al. | |
| 6,110,211 A | 8/2000 | Weiss | |
| 6,113,604 A | 9/2000 | Whittaker et al. | |
| 6,117,138 A | 9/2000 | Burrows et al. | |
| 6,117,173 A | 9/2000 | Taddia et al. | |
| 6,126,694 A | 10/2000 | Gray, Jr. | |
| 6,136,035 A | 10/2000 | Lob et al. | |
| 6,139,551 A | 10/2000 | Michelson et al. | |
| 6,143,030 A | 11/2000 | Schroder | |
| 6,152,963 A | 11/2000 | Noiles et al. | |
| RE37,005 E | 12/2000 | Michelson et al. | |
| 6,159,216 A | 12/2000 | Burkinshaw et al. | |
| 6,206,884 B1 | 3/2001 | Masini | |
| 6,224,605 B1 | 5/2001 | Anderson et al. | |
| 6,224,609 B1 | 5/2001 | Ressemann et al. | |
| 6,238,435 B1 | 5/2001 | Meulink et al. | |
| 6,245,111 B1 | 6/2001 | Shaffner | |
| 6,267,785 B1 | 7/2001 | Masini | |
| 6,302,890 B1 | 10/2001 | Leone, Jr. | |
| 6,306,174 B1 | 10/2001 | Gie et al. | |
| 6,325,804 B1 | 12/2001 | Wenstrom, Jr. et al. | |
| 6,330,845 B1 | 12/2001 | Meulink | |
| 6,338,734 B1 | 1/2002 | Burke et al. | |
| 6,344,060 B1 | 2/2002 | Schmotzer et al. | |
| 6,361,565 B1 | 3/2002 | Bonutti | |
| 6,371,991 B1 | 4/2002 | Manasas et al. | |
| 6,379,384 B1 | 4/2002 | Mckernan et al. | |
| 6,395,004 B1 | 5/2002 | Dye et al. | |
| 6,468,281 B1 | 10/2002 | Bädorf et al. | |
| 6,517,581 B2 | 2/2003 | Blamey | |
| 6,626,913 B1 | 9/2003 | Mckinnon et al. | |
| 6,871,549 B2 | 3/2005 | Serra et al. | |
| 6,875,239 B2 | 4/2005 | Gerbec et al. | |
| 6,883,217 B2 | 4/2005 | Barrette et al. | |
| 6,913,623 B1 | 7/2005 | Zhu | |
| 6,932,819 B2 | 8/2005 | Wahl et al. | |
| 7,074,224 B2 | 7/2006 | Daniels et al. | |
| 7,179,259 B1 | 2/2007 | Gibbs | |
| 7,210,881 B2 | 5/2007 | Greenberg | |
| 7,247,171 B2 | 7/2007 | Sotereanos | |
| 7,255,716 B2 | 8/2007 | Pubols et al. | |
| 7,261,741 B2 | 8/2007 | Weissman et al. | |
| 7,291,176 B2 | 11/2007 | Serra et al. | |
| 7,296,804 B2 | 11/2007 | Lechot et al. | |
| 7,297,166 B2 | 11/2007 | Dwyer et al. | |
| 7,341,589 B2 | 3/2008 | Weaver et al. | |
| 7,425,214 B1 | 9/2008 | McCarthy et al. | |
| 7,491,242 B2 | 2/2009 | Pichon et al. | |
| 7,582,092 B2 | 9/2009 | Jones | |
| 7,585,301 B2 | 9/2009 | Santarella et al. | |
| 7,585,329 B2 | 9/2009 | Mccleary et al. | |
| 7,832,405 B1 | 11/2010 | Schlueter et al. | |
| 7,857,858 B2 | 12/2010 | Justin et al. | |
| 7,887,539 B2 | 2/2011 | Dunbar, Jr. | |
| 8,118,868 B2 | 2/2012 | May et al. | |
| 8,221,432 B2 | 7/2012 | Smith et al. | |
| 8,226,725 B2 | 7/2012 | Ferko | |
| 8,333,807 B2 | 12/2012 | Smith et al. | |
| 8,419,743 B2 | 4/2013 | Smith | |
| 8,460,393 B2 | 6/2013 | Smith et al. | |
| 8,529,569 B2 | 9/2013 | Smith et al. | |
| 8,679,130 B2 | 3/2014 | Smith et al. | |
| 8,876,837 B2 | 11/2014 | Smith et al. | |
| 8,906,109 B2 | 12/2014 | Smith et al. | |
| 9,510,950 B2 | 12/2016 | Smith et al. | |
| 2003/0233100 A1 | 12/2003 | Santarella et al. | |
| 2004/0107001 A1 | 6/2004 | Cheal et al. | |

(56) References Cited

U.S. PATENT DOCUMENTS

| | | |
|---|---|---|
| 2004/0122439 A1 | 6/2004 | Dwyer et al. |
| 2004/0236341 A1 | 11/2004 | Petersen |
| 2004/0267267 A1 | 12/2004 | Daniels |
| 2005/0149042 A1 | 7/2005 | Metzger |
| 2005/0203539 A1 | 9/2005 | Grimm et al. |
| 2005/0234463 A1 | 10/2005 | Hershberger |
| 2006/0004459 A1 | 1/2006 | Hazebrouck et al. |
| 2007/0093844 A1 | 4/2007 | Dye |
| 2007/0123908 A1 | 5/2007 | Jones et al. |
| 2007/0129809 A1 | 6/2007 | Meridew et al. |
| 2007/0233127 A1 | 10/2007 | Tuke et al. |
| 2008/0125867 A1 | 5/2008 | Mccleary et al. |
| 2008/0154276 A1 | 6/2008 | Pubols et al. |
| 2008/0161811 A1 | 7/2008 | Daniels et al. |
| 2008/0177393 A1* | 7/2008 | Grant .................. A61F 2/30734 623/18.11 |
| 2008/0208203 A1 | 8/2008 | Moindreau et al. |
| 2008/0234685 A1 | 9/2008 | Gjerde |
| 2008/0243133 A1 | 10/2008 | Heinz |
| 2008/0243190 A1 | 10/2008 | Dziedzic et al. |
| 2008/0269765 A1 | 10/2008 | Banerjee et al. |
| 2008/0281428 A1 | 11/2008 | Meyers et al. |
| 2008/0294168 A1 | 11/2008 | Wieland |
| 2009/0099566 A1 | 4/2009 | Maness et al. |
| 2009/0112218 A1 | 4/2009 | Mccleary et al. |
| 2009/0265014 A1 | 10/2009 | May et al. |
| 2009/0270866 A1 | 10/2009 | Poncet |
| 2011/0015634 A1 | 1/2011 | Smith et al. |
| 2011/0046745 A1 | 2/2011 | Daniels et al. |
| 2011/0218537 A1 | 9/2011 | Smith et al. |
| 2011/0218583 A1 | 9/2011 | Smith et al. |
| 2011/0218636 A1 | 9/2011 | Smith et al. |
| 2011/0218641 A1 | 9/2011 | Smith et al. |
| 2012/0226282 A1 | 9/2012 | Smith et al. |
| 2013/0110185 A1 | 5/2013 | Smith |
| 2013/0231674 A1 | 9/2013 | Smith et al. |
| 2013/0274889 A1 | 10/2013 | Smith et al. |
| 2014/0012268 A1 | 1/2014 | Smith et al. |
| 2014/0081272 A1 | 3/2014 | Smith et al. |
| 2014/0200619 A1 | 7/2014 | Smith et al. |
| 2015/0038972 A1 | 2/2015 | Smith et al. |
| 2015/0094820 A1 | 4/2015 | Smith et al. |

FOREIGN PATENT DOCUMENTS

| | | |
|---|---|---|
| EP | 0453695 A1 | 10/1991 |
| FR | 2676172 A1 | 11/1992 |
| FR | 2732891 A1 | 10/1996 |
| FR | 2792822 A1 | 11/2000 |
| GB | 2299758 A | 10/1996 |
| WO | WO-9421199 A1 | 9/1994 |
| WO | WO-2007106752 A2 | 9/2007 |

OTHER PUBLICATIONS

"U.S. Appl. No. 12/718,230, Notice of Allowance dated Feb. 13, 2013", 5 pgs.

"U.S. Appl. No. 12/718,230, Response filed Feb. 6, 2013 to Non Final Office Action dated Nov. 7, 2012", 14 pgs.

"U.S. Appl. No. 12/718,230, Response filed Aug. 17, 2012 to Restriction Requirement dated Jul. 19, 2012", 4 pgs.

"U.S. Appl. No. 12/718,230, Restriction Requirement dated Jul. 19, 2012", 6 pgs.

"U.S. Appl. No. 12/718,230, Supplemental Amendment filed Oct. 23, 2012", 14 pgs.

"U.S. Appl. No. 13/913,858, Applicant's Summary of Examiner Interview filed Jul. 10, 2014", 2 pgs.

"U.S. Appl. No. 13/913,858, Applicant's Summary of Examiner Interview filed Jul. 24, 2014", 2 pgs.

"U.S. Appl. No. 13/913,858, Notice of Allowance dated Aug. 4, 2015", 18 pgs.

"U.S. Appl. No. 14/563,118, Non Final Office Action dated Oct. 20, 2015", 19 pgs.

"U.S. Appl. No. 14/563,118, Notice of Allowance dated Aug. 1, 2016", 11 pgs.

"U.S. Appl. No. 14/563,118, Response filed Apr. 20, 2016 to Non Final Office Action dated Oct. 20, 2015", 15 pgs.

"U.S. Appl. No. 14/563,118, Response filed Jul. 27, 2015 to Restriction Requirement dated Jun. 8, 2015", 7 pgs.

"U.S. Appl. No. 14/563,118, Restriction Requirement dated Jun. 8, 2015", 6 pgs.

"Arcos Modular Femoral Revisions System Surgical Techniques", Biomet Orthopedics, (2010), 96 pgs.

"REEF: Distally Interlocked Modular Femoral Reconstruction Prosthesis", Johnson & Johnson company, (2004), 7 pgs.

"ZMR Hip System", Product Brochure, Zimmer, Inc., (2004, 2008, 2009), 19 pgs.

* cited by examiner

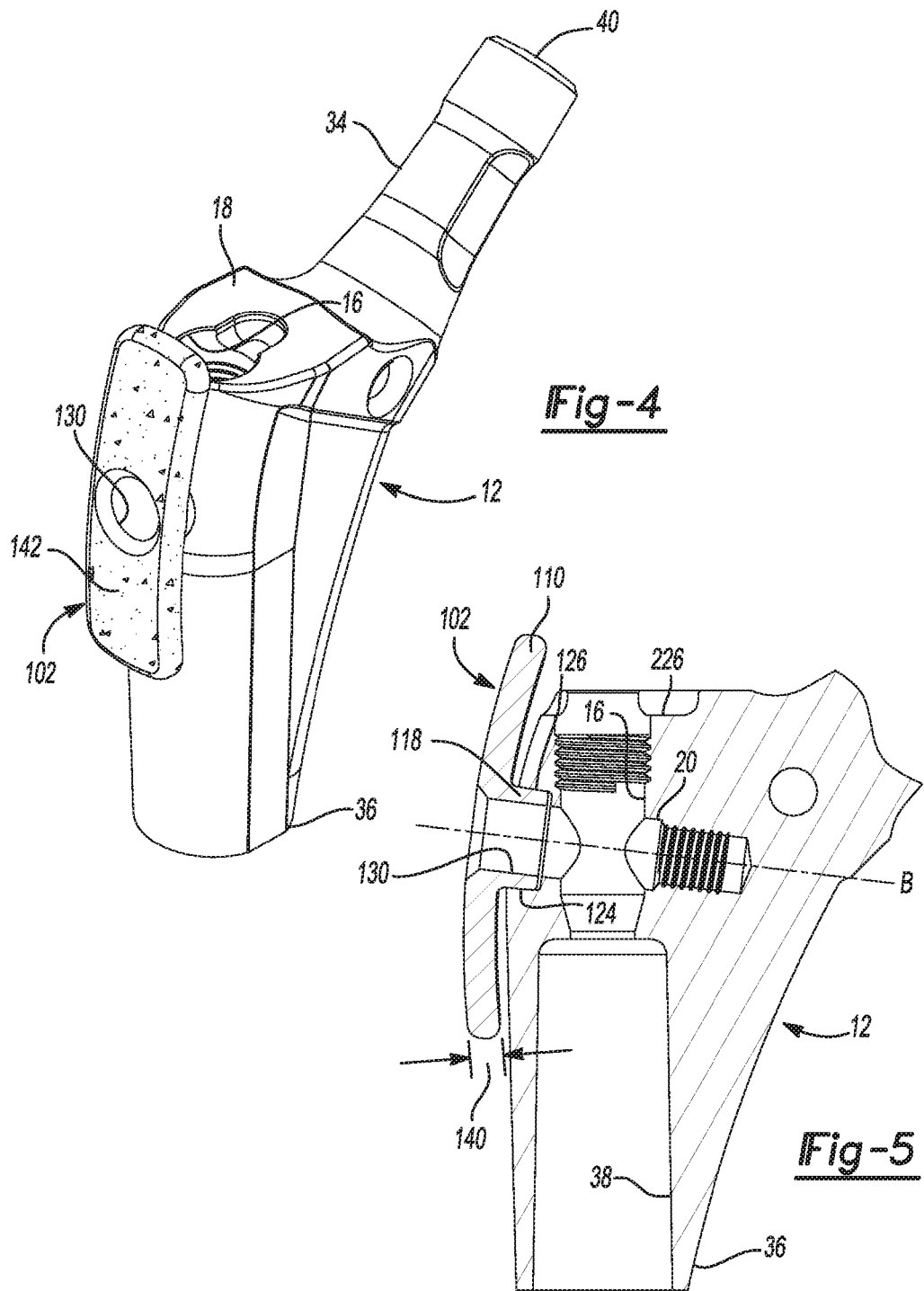

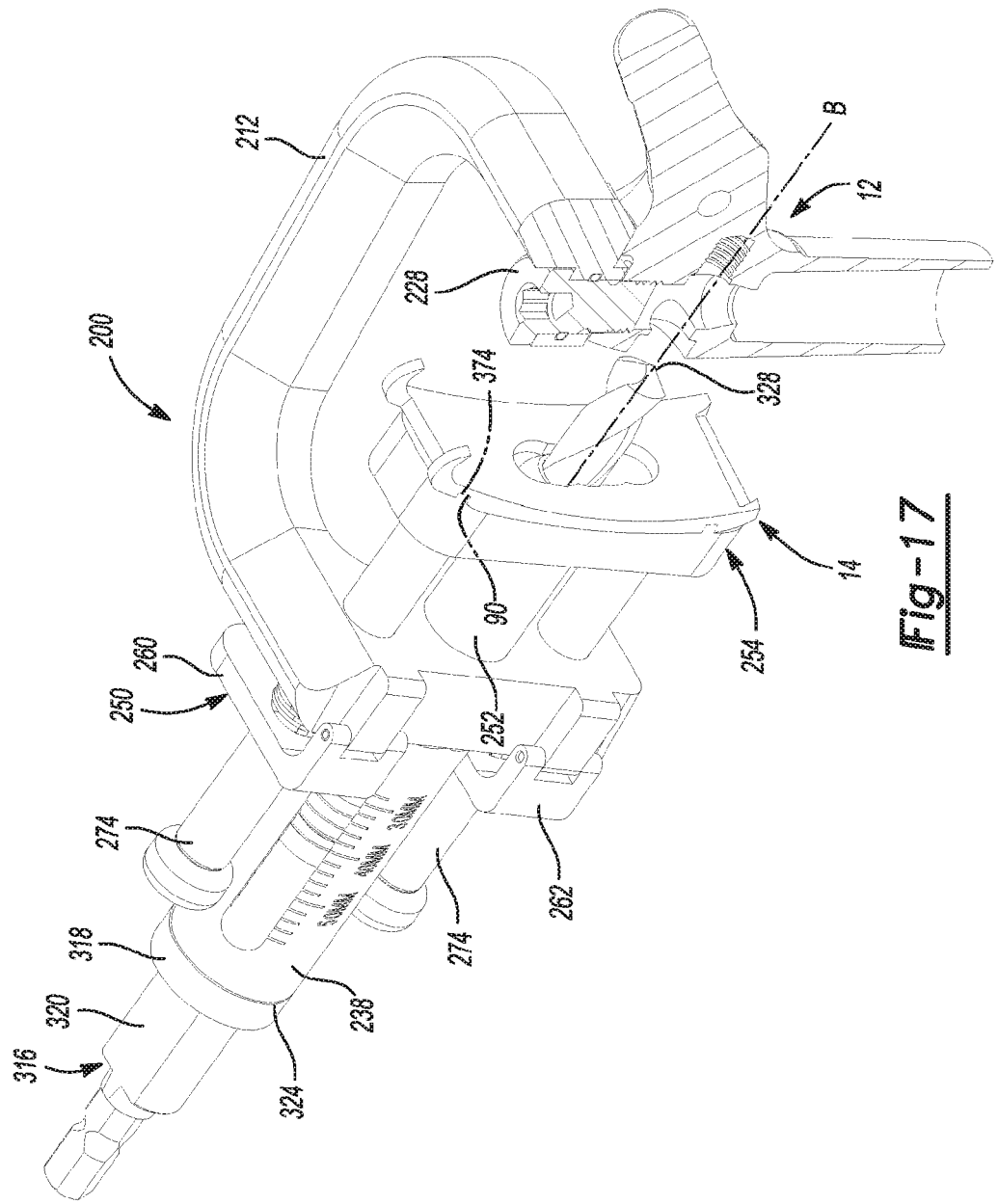

MODULAR LATERAL HIP AUGMENTS

CROSS-REFERENCE TO RELATED APPLICATIONS

This application is a continuation of U.S. patent application Ser. No. 14/563,118, filed on Dec. 8, 2014, now U.S. Pat. No. 9,510,950, which is a divisional of U.S. patent application Ser. No. 13/913,858, filed on Jun. 10, 2013, now U.S. Pat. No. 8,906,109, which is a divisional of U.S. patent application Ser. No. 12/718,230, filed on Mar. 5, 2010, now U.S. Pat. No. 5,460,393. The entire disclosure(s) of (each of) the above application(s) is (are) incorporated herein by reference.

This application is also related to U.S. patent application Ser. No. 12/718,018, now U.S. Pat. No. 8,221,432, issued Jul. 17, 2012, entitled "METHOD AND APPARATUS FOR IMPLANTING A MODULAR FEMORAL HIP;" U.S. patent application Ser. No. 12/718,023, entitled "GUIDE ASSEMBLY FOR LATERAL IMPLANTS AND ASSOCIATED METHODS;" U.S. patent application Ser. No. 12/718,026, entitled "REVISION BROACH WITH SMOOTH LATERAL SIDE;" U.S. patent application Ser. No. 12/718,027, now U.S. Pat. No. 8,419,743, issued Apr. 16, 2013, entitled "ASSEMBLY TOOL FOR MODULAR IMPLANTS AND ASSOCIATED METHOD;" and U.S. patent application Ser. No. 12/718,031, now U.S. Pat. No. 8,333,807, issued Dec. 18, 2012, entitled "METHOD AND APPARATUS FOR TRIALING AND IMPLANTING A MODULAR FEMORAL HIP;" each filed concurrently with U.S. patent application Ser. No. 12/718,230, filed on Mar. 5, 2010. The disclosures of each of the above applications are incorporated herein by reference.

FIELD

The present teachings relate generally to lateral augment implants for use with a hip implant.

BACKGROUND

The statements in this section merely provide background information related to the present disclosure and may not constitute prior art.

In many reconstructive procedures of the hip joint, the greater trochanter can sometimes be resected from the proximal femur to provide access to the joint or a primary hip prosthesis, such as during a revision hip replacement procedure. The resected portion of the greater trochanter can be reattached after a revision femoral prosthetic component is implanted using, for example, bolts, wires, nails, etc. either alone or in combination. The greater trochanter may also fracture unintentionally during the insertion of a prosthetic implant and may require reattachment. Further, the greater trochanter may need to be partially resected and/or may include bone loss due to, for example, wear over time. In such circumstances, the greater trochanter may require additional support to compensate for the area of bone loss.

There is, therefore, a need for improved implants and associated guide instruments that facilitate lateral access to a hip prosthesis and allow easy alignment, insertion and removal of trochanteric bolts.

SUMMARY

This section provides a general summary of the disclosure, and is not a comprehensive disclosure of its full scope or all of its features.

In one form, an implant for a hip is provided and can include a lateral augment adapted to be coupled to a lateral side of a femoral body implant. The lateral augment can include a body portion having a first surface, a second surface opposite the first surface, and a protrusion extending from the second surface. The protrusion can have a shape adapted to mate with a complementary shaped recess formed in the lateral side of the proximal femoral body implant. The lateral augment can further include an aperture and a fastener received through the aperture. The aperture can be positioned in the body portion and extend through the protrusion such that the aperture is adapted to be coaxially aligned with the lateral bore in the femoral body implant. The fastener can be adapted to be threadably secured to the lateral bore and configured to have a length sufficient to pass through a portion of a greater trochanter for securing the portion of the greater trochanter and the lateral augment to the femoral body implant.

In another form, an implant for a hip is provided and can include a lateral augment adapted to be coupled to a lateral side of a proximal femoral body implant. The lateral augment can include a body portion having a first surface and a second surface opposite the first surface and adapted to be positioned adjacent to the lateral side of the proximal femoral body implant such that a portion of the body portion extends beyond a proximal end of the proximal femoral body implant. An aperture can be positioned in the body portion at a proximal region and extend through the body portion. At least one bore can be positioned in the body portion and be spaced apart from the aperture and adapted to be above a proximal end of the proximal femoral body implant when the lateral augment is coupled thereto. The implant can further include a first fastener configured to be received in the bore of the body portion and adapted to secure soft tissue thereto, and a ligament washer can be received by the first fastener and have at least one soft tissue engagement member adapted to engage the soft tissue. A second fastener can be received through the aperture and can be adapted to be threadably secured to a lateral bore in the proximal femoral body implant.

Further areas of applicability will become apparent from the description provided herein. It should be understood that the description and specific examples are intended for purposes of illustration only and are not intended to limit the scope of the present teachings.

DRAWINGS

The present teachings will become more fully understood from the detailed description, the appended claims and the following drawings. The drawings are for illustrative purposes only and are not intended to limit the scope of the present disclosure.

FIG. 4 is a perspective view of an implant body with an exemplary lateral augment according to the present teachings;

FIG. 5 is a sectional view of FIG. 4 according to the present teachings;

FIGS. 15-20B are sequential perspective views of the exemplary guide assembly illustrating use of the guide assembly in various stages of engagement and with alternative combinations of implants according to the present teachings;

DETAILED DESCRIPTION

Figure 1:
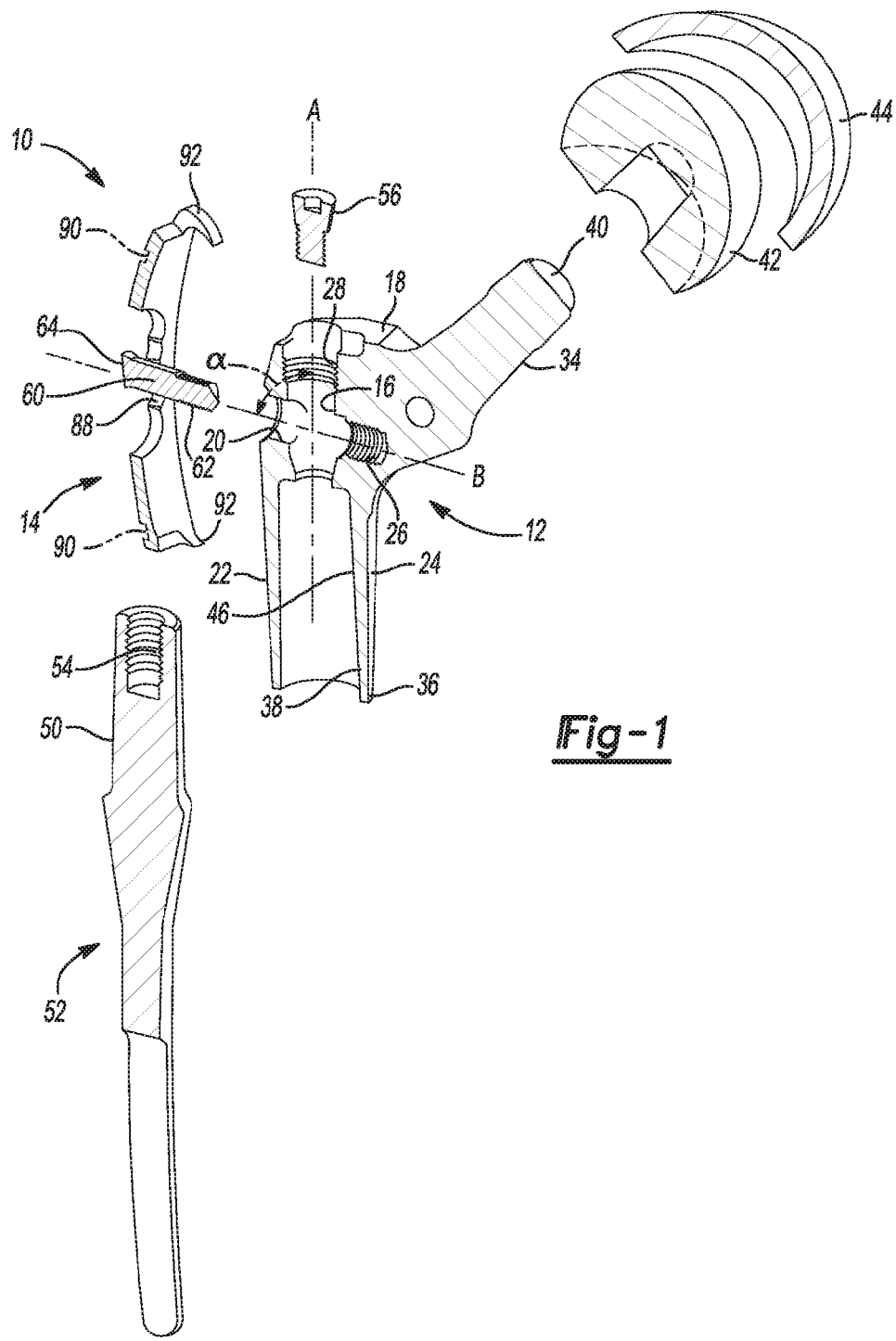
FIG. 1 is an exploded sectional view of an exemplary implant according to the present teachings.

The following description is merely exemplary in nature and is not intended to limit the present disclosure, its application, or uses. It should be understood that throughout the drawings, corresponding reference numerals indicate like or corresponding parts and features. In particular, the guide assembly of the present teachings can be used with any type of prosthesis for a bone, such as, for example, a proximal or distal femur, a proximal or distal tibia, a proximal or distal humerus, etc. Similarly, the lateral implants can include various types of implants such as, for example, a lateral augment or a claw plate, or combinations thereof. Therefore, it will be understood that the following discussions are not intended to limit the scope of the appended claims.

Figure 2:
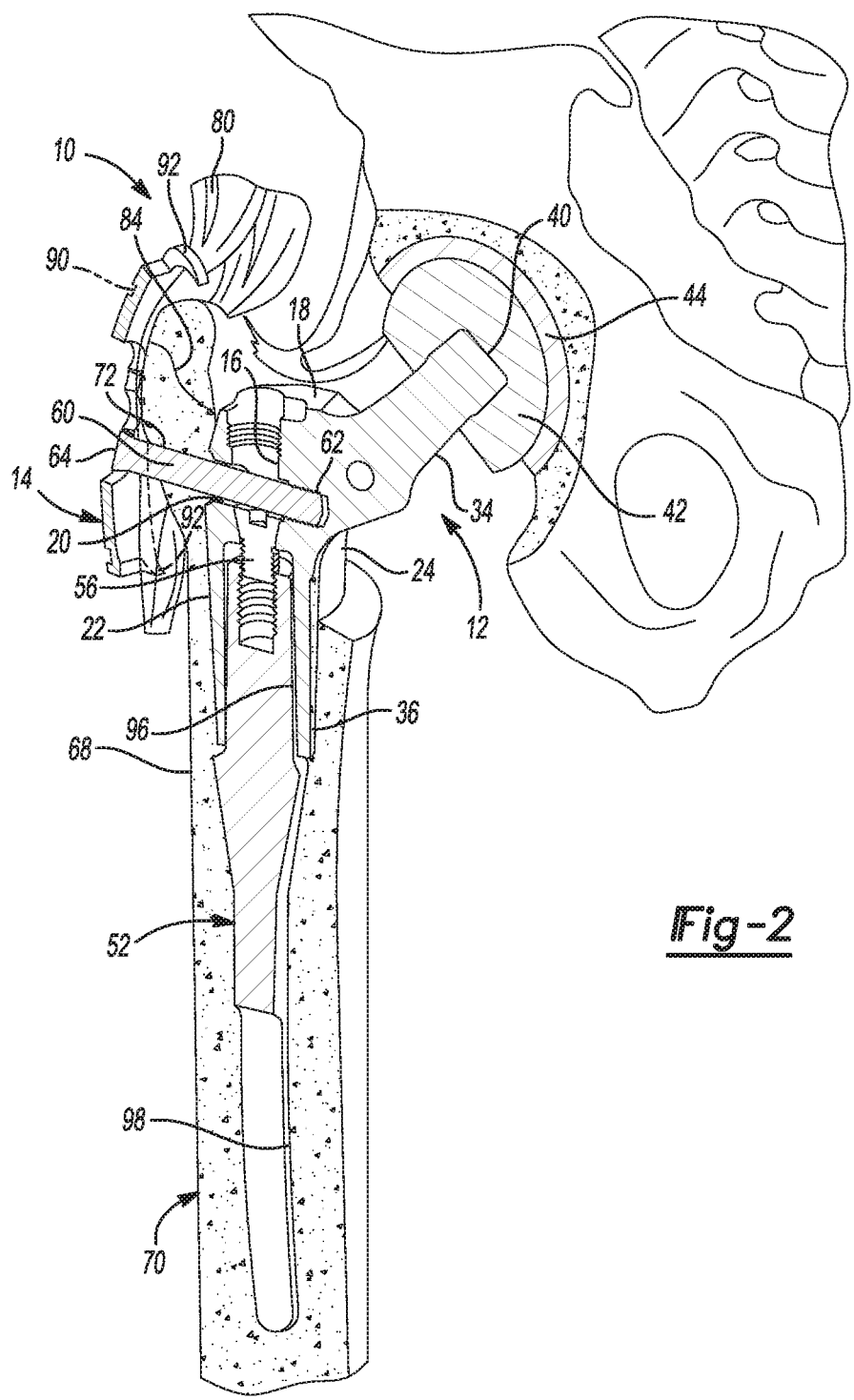
FIG. 2 is a sectional environmental view of the implant of FIG. 1 according to the present teachings.

Referring initially to FIGS. 1 and 2, an exemplary implant 10 according to the present teachings can include a proximal femoral body implant 12 and a lateral support implant or claw plate 14. The proximal femoral body 12 can define a longitudinal bore 16 extending from a proximal end 18 along a longitudinal axis A and a blind bore 20 extending from a lateral side 22 towards a medial side 24 without surfacing on medial side 24 and having a longitudinal axis B. Blind bore 20 can be positioned at an acute angle α relative to longitudinal axis A. While blind bore 20 is shown as extending at an acute angle relative to longitudinal axis A, it should be appreciated that angle α can include various angles as may be desirable for different femoral body implant configurations. Bore 20 can include a threaded portion 26 and longitudinal bore 16 can also include a threaded portion 28 adjacent proximal end 18.

Proximal femoral body 12 can also include a neck portion 34 and a distal end 36 having a bore 38. Neck portion 34 can include a distal end 40 for receiving a spherical femoral head 42 that can mate with an acetabular cup 44, as shown in FIGS. 1 and 2. The femoral head 42 can be coupled to the neck portion 34 with a tapered connection, such as a Morse taper connection. Distal end bore 38 can include a female tapered configuration 46 that is configured to matingly receive a corresponding proximal male tapered end 50 of a distal stem extension 52 of implant 10. Tapered end 50 can include a blind threaded bore 54 configured to receive fastener 56 therein.

The implant 10 can further include a lateral fastener, such as a trochanteric bolt 60, having a threaded end 62 and a head 64. Trochanteric bolt 60 can be inserted into the lateral blind bore 20 from a lateral side 68 of the femur 70 through a lateral bore 72 drilled into femur 70. Lateral bore 72 can be coaxial with blind bore 20 and can be drilled into femur 70 using guide assembly 200 of FIG. 10, as will be described in more detail below. The threaded end 62 of trochanteric bolt 60 can engage threaded portion 26 of blind bore 20.

The claw plate 14 can be implanted laterally in soft tissue 80 adjacent to the femur 70 with the assistance of the guide assembly 200, as will also be described below in greater detail. Claw plate 14 can be used to provide support for soft tissue and/or a bone fragment, such as a portion 84 of a greater trochanter that has been broken off or resected, which may be required during a revision hip replacement procedure. The claw plate 14 can be retained in position by the head 64 of trochanteric bolt 60, with the head 64 being received in a countersunk bore 88 of claw plate 14, as shown in FIGS. 1-3. The claw plate 14 can have a variety of shapes depending on the particular application and can also be anatomically configured so as to have a shape that substantially conforms to the shape of the lateral side 68 of the femur 70 or the greater trochanter bone portion 84. The claw plate 14 can also include anchors or soft tissue piercing spikes 92 for soft tissue attachment.

With particular reference to FIG. 2, the proximal femoral body 12 can be coupled to the distal stem extension 52 with a Morse taper connection 96 such that the tapered proximal end 50 of the stem extension 52 is press fitted into the tapered distal bore 38 of proximal femoral body 12. The proximal femoral body 12 can be at least partially received in an intramedullary canal 98 of the femur 70. The distal stem extension 52 can also be locked to the proximal body 12 by fastener 56 being received in longitudinal bore 16 of proximal body 12 and engaging threaded bore 54 of stem extension 52. The proximal femoral body 12 and distal stem 52 can be implanted using a minimally invasive procedure or technique through a small anterior or posterior incision adjacent the left or right femur.

Referring additionally to FIGS. 3-9, implant 10 can also include lateral augments, such as lateral augments 102, 104, as may be required during a revision hip replacement procedure to provide for proper trochanter attachment. For example, if a portion of the greater trochanter needs to be resected and/or removed during a revision hip procedure to provide for removal of a primary hip implant, the augments 102, 104 can act as spacers to provide appropriate adjustment for the location of attachment of the trochanter to the proximal femoral body 12, as shown for example in FIG. 3A. The lateral augments 102, 104 can also be used during a revision hip replacement procedure to compensate for any bone loss adjacent the lateral side of the hip implant.

Figure 3A:
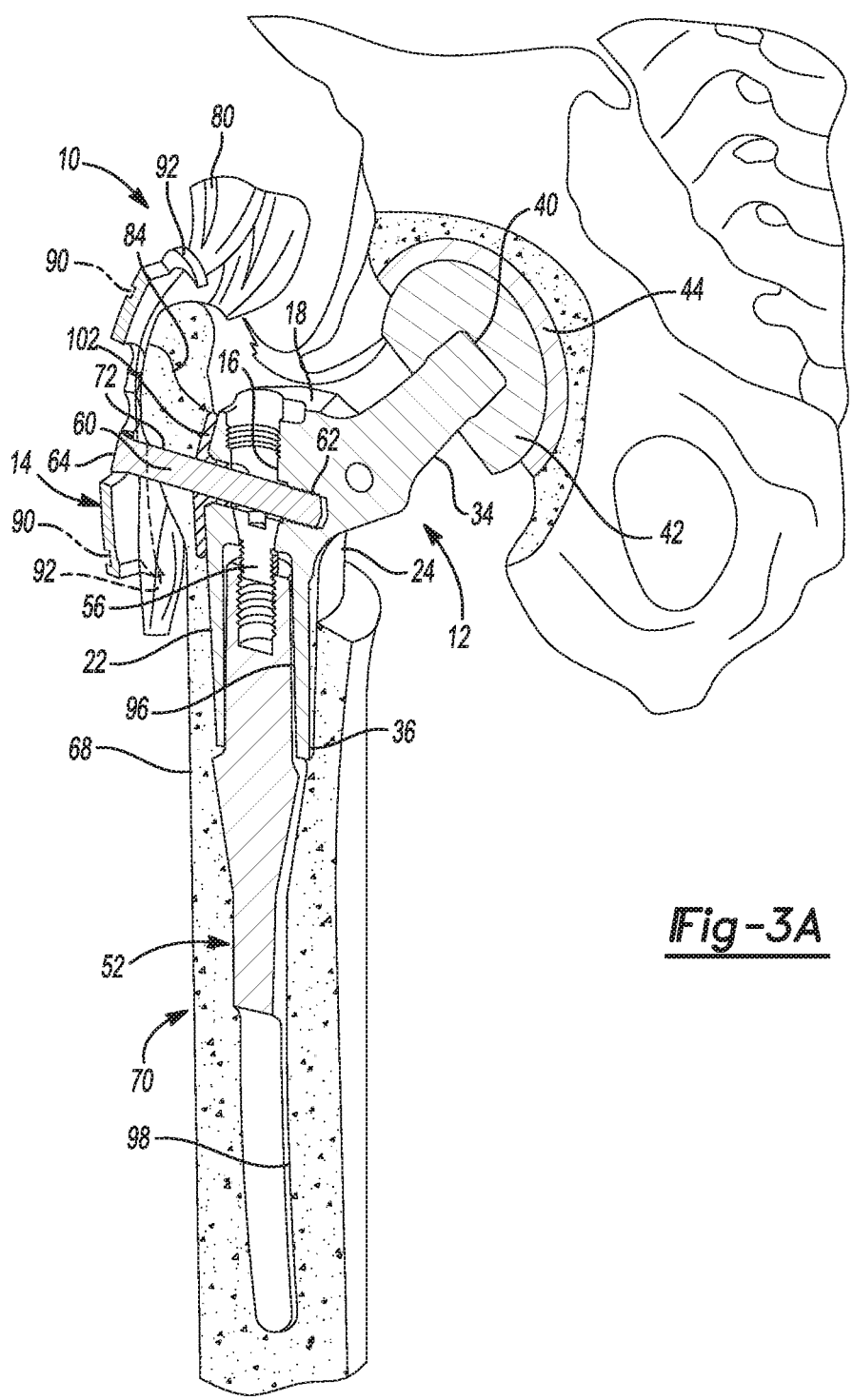
FIG. 3A is a sectional environmental view of the implant of FIG. 1 with an exemplary lateral augment according to the present teachings.

With particular reference to FIGS. 3A-6B, lateral augment 102 can include a substantially T-shaped configuration 108 having a body portion 110 with a lateral bone engaging surface 112 and a medial implant facing surface 114, and a cylindrical or tubular portion 118 extending from medial surface 114. Tubular portion 118 can include a tapered exterior surface 120 configured to be received in a mating tapered counterbore 124 formed into proximal femoral implant body 12, as generally shown in FIG. 5. The tapered exterior surface 120 and corresponding tapered counterbore 124 can be configured to provide a Morse taper connection 126 for coupling lateral augment 102 to proximal femoral body 12. Augment 102 can include an aperture 130 extending through body portion 110 and tubular portion 118 for receiving trochanter bolt 60 to secure claw plate 14 and T-shaped augment 102 to proximal femoral body 12, as generally shown in FIG. 3A.

Lateral augment 102 can further include a generally arcuate shape 136 corresponding to a mating shape on lateral side 68 of proximal femoral body 12. Lateral augment 102 can be configured with various lengths 138 and thicknesses 140, as may be required to provide for appropriate trochanter positioning and attachment during the revision hip procedure discussed above. Lateral surface 112 can also be provided with a roughened or porous metal coating to enhance biologic fixation, such as a layer of Regenerex® porous titanium construct 142, available from Biomet, Inc. of Warsaw, Ind. Alternatively, lateral augment 102 can be formed entirely out of porous metal.

Figure 7:
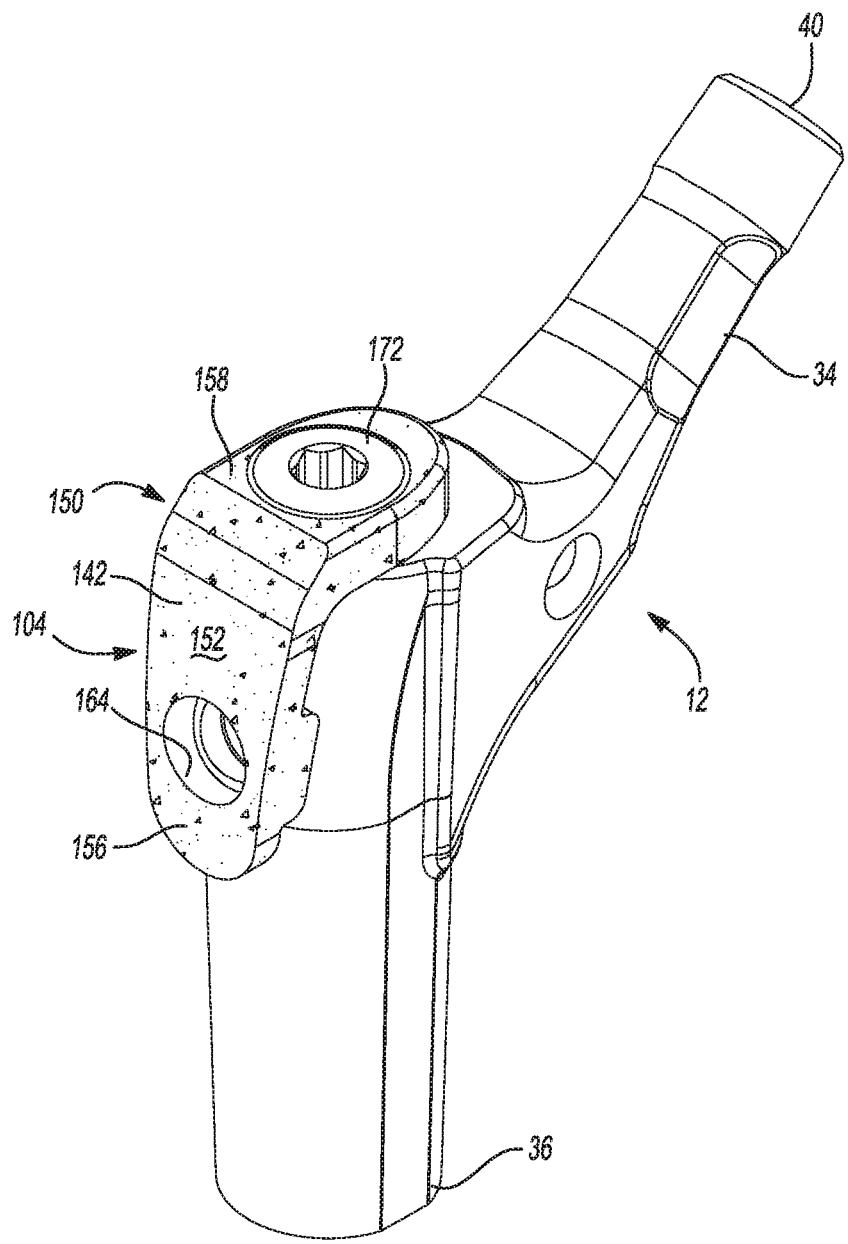
FIG. 7 is a perspective view of an implant body with an exemplary lateral augment according to the present teachings.
Figure 8:
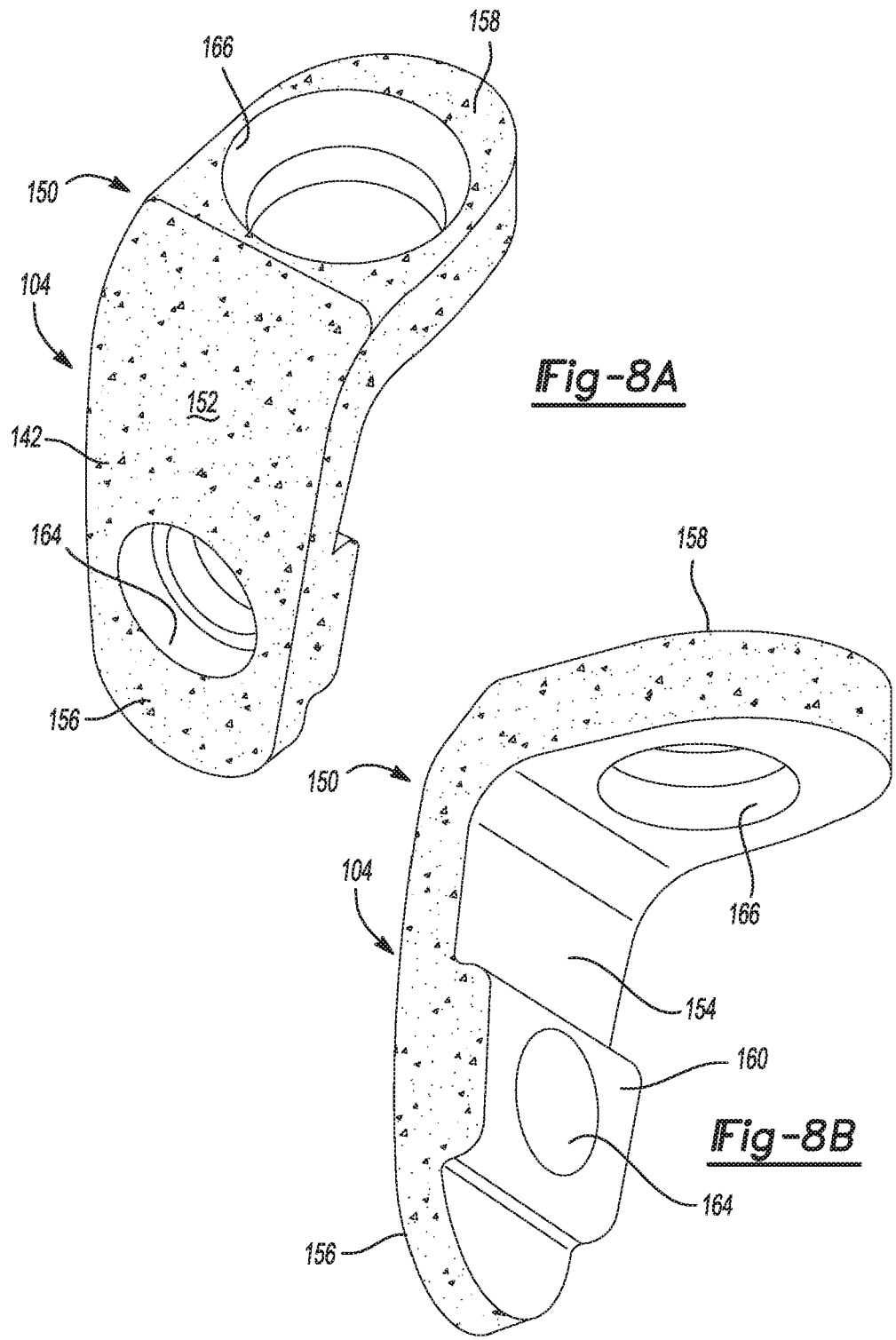
FIGS. 8A and 8B are lateral and medial perspective views of the exemplary lateral augment of FIG. 7 according to the present teachings.
Figure 9:
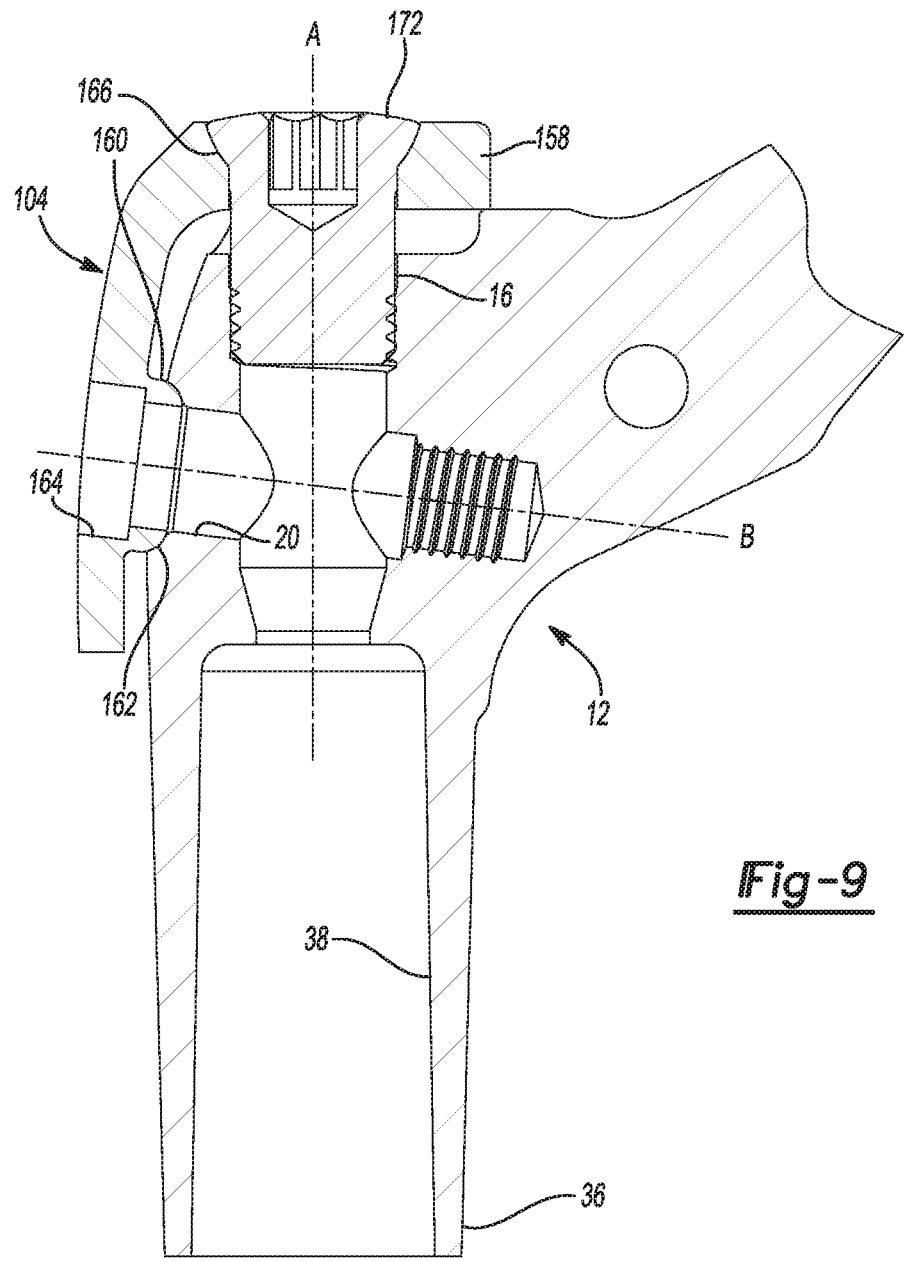
FIG. 9 is a sectional view of FIG. 7 according to the present teachings.

Referring now to FIGS. 7-9, lateral augment 104 can include an L-shaped configuration 150 with a lateral surface 152, a medial surface 154, a lateral portion 156 and a superior portion 158 extending from lateral portion 156. Lateral surface 152 can include a layer of porous metal coating, such as the layer of Regenerex® 142 discussed above and as generally shown in FIG. 8A. In an alternative configuration, lateral augment 104 can be formed entirely out of porous metal. Lateral portion 156 can include a protrusion 160 extending from rear surface 154 and configured to engage a correspondingly shaped recess 162 in the proximal femoral body 12, as shown in FIGS. 8B and 9.

Figure 3B:
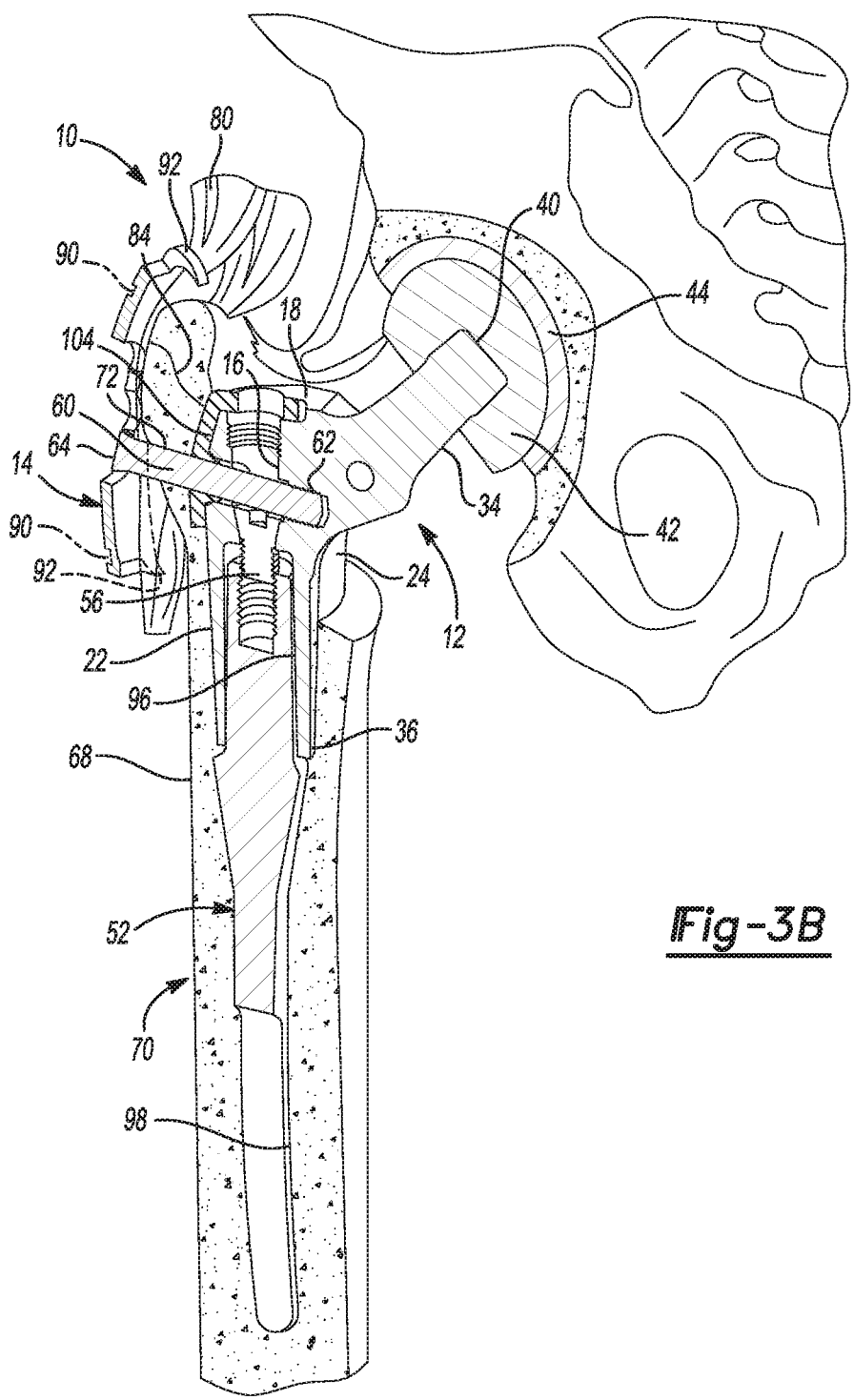
FIG. 3B is a sectional environmental view of the implant of FIG. 1 with another exemplary lateral augment according to the present teachings.
Figure 6A:
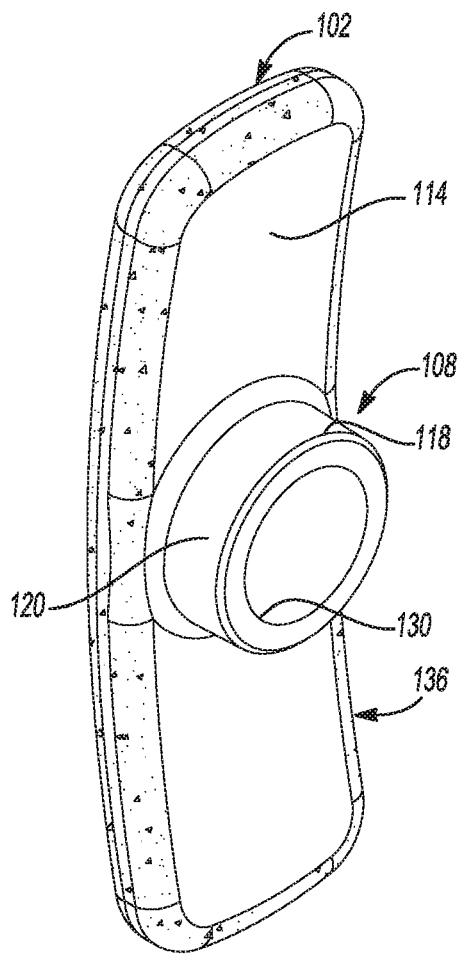
FIG. 6A is a medial perspective view of the exemplary lateral augment of FIG. 4 according to the present teachings.
Figure 6B:
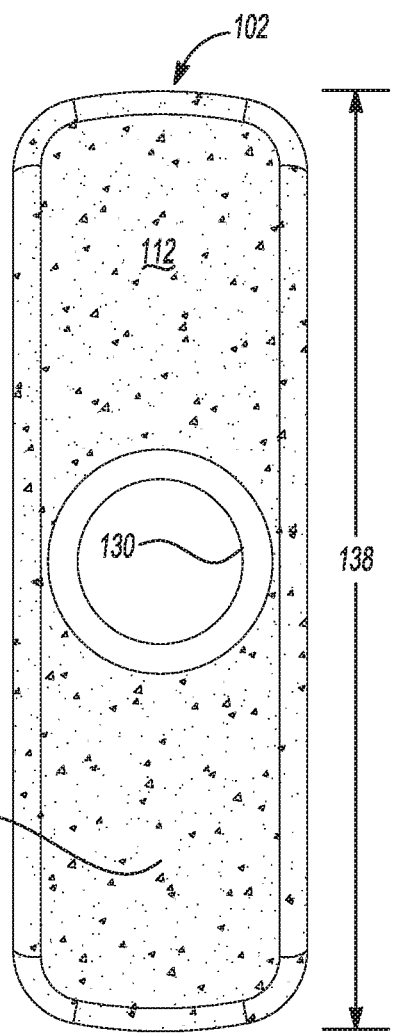
FIG. 6B is a lateral view of the exemplary lateral augment of FIG. 4 according to the present teachings.

A first aperture 164 can be provided in lateral portion 156 and a second aperture 166 can be provided in top portion 158 such that when the L-shaped augment 104 is positioned on proximal femoral body 12, the first aperture 164 can be coaxially aligned with blind bore 20 and the second aperture 166 can be coaxially aligned with longitudinal bore 16, as shown in FIG. 9. Trochanter bolt 60 can be received through claw plate 14 and first aperture 164 and threadingly engaged with threaded bore 20 to couple claw plate 14 and lateral portion 156 to proximal femoral body 12, as generally shown in FIG. 3B. Second aperture 166 can receive a fastener 172 to secure superior portion 158 to proximal end 18 of proximal femoral body 12.

Referring now to FIGS. 10-14, and with continuing reference to FIGS. 1-9, after the proximal femoral body 12 has been implanted, as well as the T-shaped or L-shaped lateral augments 102 or 104 attached as may be required, the claw plate 14 can be implanted using guide assembly 200. In the exemplary application of a revision hip replacement, guide assembly 200 can provide for forming the lateral bore 72 and inserting the trochanteric bolt 60 therethrough and into engagement with the proximal femoral body 12 after the proximal body has been implanted in femur 70.

Figure 10:
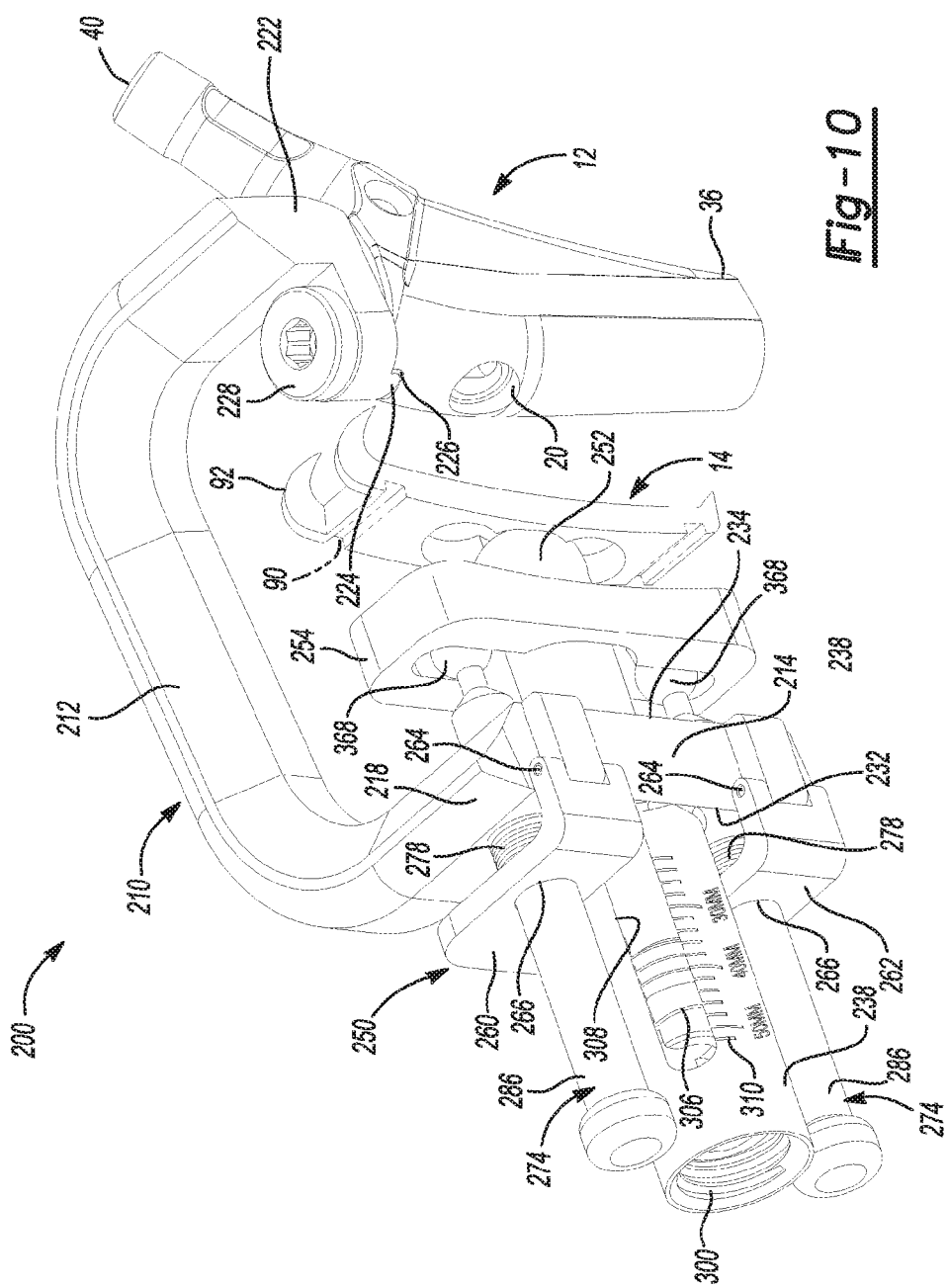
FIGS. 10 and 10A are perspective views of an exemplary guide assembly with a left-handed outrigger coupled to an associated implant according to the present teachings.

Guide assembly 200 can include an exemplary left-handed outrigger 210 that can take the form of a C-shaped arm 212, a leg or base portion 214 extending from a first or lateral end 218 of C-shaped arm 212, and a bore 220 (FIG. 13) extending through a second or medial end 222 of C-shaped arm 212. Outrigger 210 can be sized to be substantially rigid so as to avoid misalignment due to bending or flexing, and can be configured with the C-shape 212 to avoid the abductor muscles 223 of the hip joint during implantation of the trochanter bolt 60, claw plate 14 and one of the lateral augments 102, 104, if required. The left-handed outrigger 210 can be used laterally with anterior incisions of the left femur area or posterior incisions of the right femur area. It will be appreciated that while outrigger 210 is shown in FIG. 10 as well as all other applicable Figures in a "left-handed" configuration, the outrigger 210 can also be configured in a "right handed" configuration, which is a mirror image of the "left handed" outrigger 210. The right-handed outrigger can be used laterally with anterior incisions of the right femur area and/or posterior incisions of the left femur area. Therefore, it will be understood that while the remaining description will focus on the left-handed outrigger 210, the description is similarly applicable to the mirror-image right-handed outrigger.

Figure 10A:
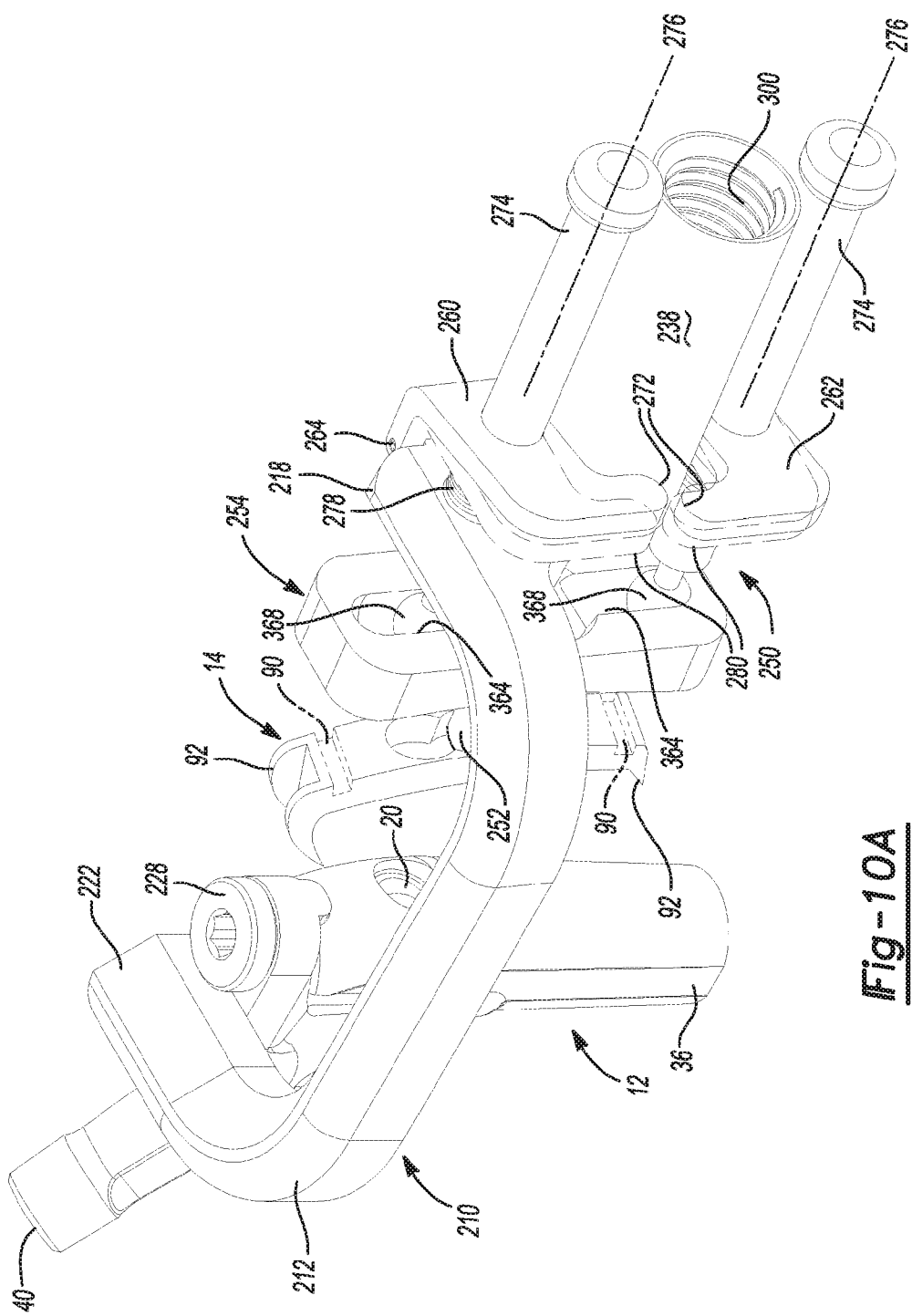
Figure 13:
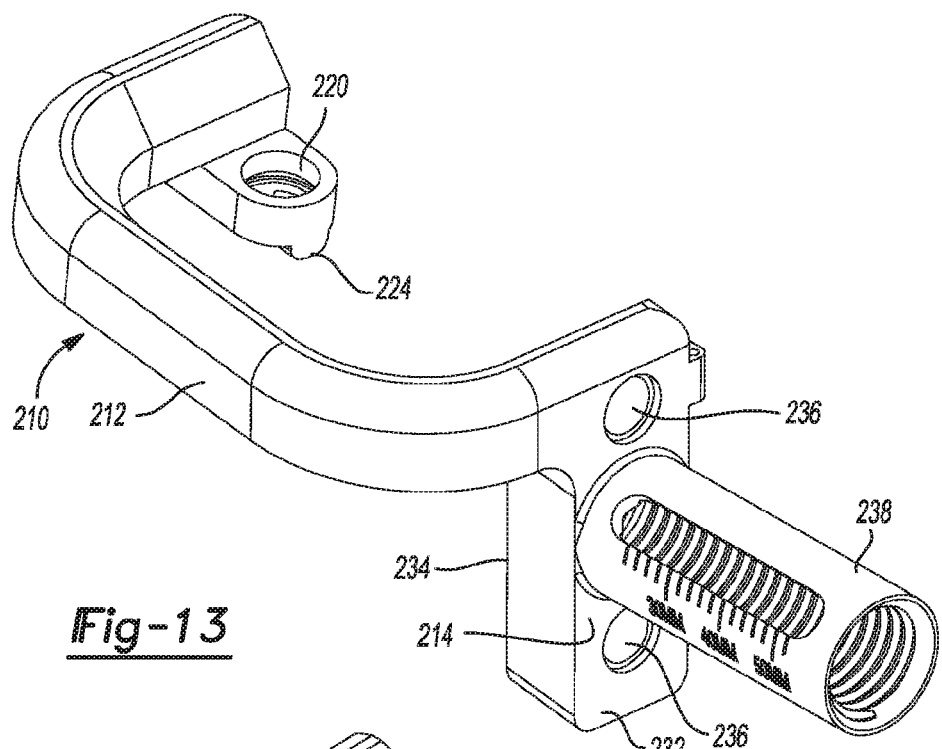
FIG. 13 is a perspective view of the left-handed outrigger according to the present teachings.
Figure 14:
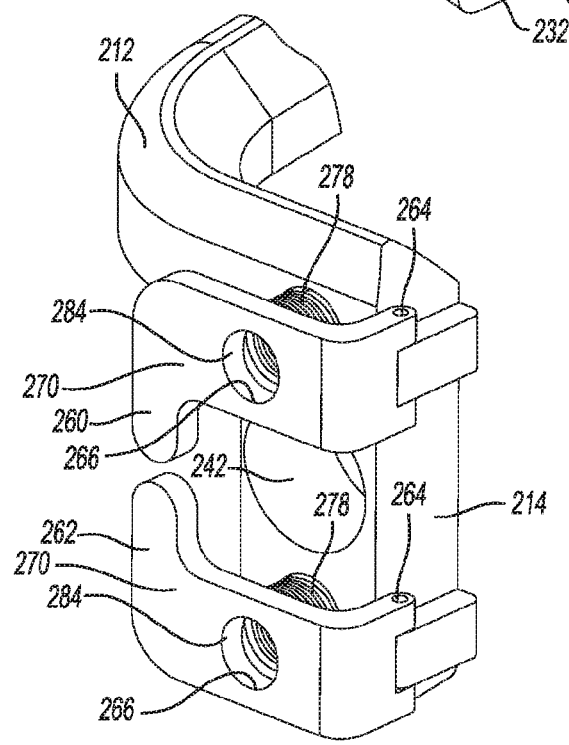
FIG. 14 is a partial perspective view of the guide assembly of FIG. 10 according to the present teachings.

Medial end 222 of C-shaped arm 212 can further include a slot-like protrusion 224 extending therefrom and configured to be received in a corresponding slot 226 positioned in proximal end 18 of femoral body 12, as shown in FIGS. 10 and 13 with reference to FIG. 5. The protrusion 224 can be used to align the guide assembly 200 to proximal femoral body 12 before coupling the C-shaped arm 212 thereto with a fastener 228, as well as to serve as an anti-rotation feature. The base portion 214 can include a lateral side 232 and a medial side 234, as well as a pair of parallel through bores 236 extending through base portion 214, as shown for example in FIG. 13. An alignment tube or sleeve 238 can be integrally formed with base portion 214 or modularly coupled thereto and can be coaxially aligned with another through bore 242 disposed in base portion 214, as shown in FIGS. 10, 10A and 14. When C-shaped arm 212 is coupled to proximal femoral body 12, base portion 214 can be parallel to longitudinal axis A and alignment tube 238 can be coaxial with longitudinal axis B of blind bore 20, as shown for example in FIG. 10.

The guide assembly 200 can also include a quick release clamp system 250, a removable sleeve 252, and a support pad 254 that cooperates with the clamp system 250 and sleeve 252. With particular reference to FIGS. 10, 10A and 14, the quick-release clamp system 250 can include first and second clamp members 260, 262 each pivotably coupled to base portion 214 via a hinge pin 264. Each of the clamp members 260, 262 can have an aperture 266 and an L-shaped configuration 270 that partially wraps around alignment tube 238, as generally shown in FIG. 10A. The apertures 266 can be co-axially aligned with respective through bores 236 in base portion 214 such that each respective aperture 266 and through bore 236 can slidably receive a cylindrical support rod 274 therethrough, as generally shown in FIGS. 10, 13 and 14. A coil spring 278 can be coupled at one end to each clamp member 260, 262 and at the other end to base portion 214, as generally shown in FIGS. 10A and 14.

The coil springs 278 can have an inner diameter sufficient for receiving one of the supports rods 274 therethrough as well as have an uncompressed length and spring force sufficient to urge respective clamp members 260, 262 away from base portion 214 to a first or locking position 272. In position 272, the clamp members 260, 262 can be positioned at a non-perpendicular angle relative to a longitudinal axis 276 of the cylindrical support rods 274, as generally shown in FIG. 10A. In this configuration, an inner surface 284 of apertures 266 can be misaligned with an exterior surface 286 of each support rod 274 so as to impinge on the support rods via the biasing force imparted by springs 278. The biasing force and resulting impingement of clamp members 260, 262 on support rods 274 serves to hold each support rod 274 in a desired fixed axial position.

To adjust a position of support rods 274 relative to clamp members 260, 262 and base portion 214, a user can depress or urge clamp members 260, 262 towards base portion 214 to a second or release position 280. In the second position 280, clamp members 260, 262 can be perpendicular or substantially perpendicular with longitudinal axis 276 and inner surfaces 284 of apertures 266 can be aligned with support rods 274. In this configuration, support rods 274 can be slidably axially translated relative to the respective clamp member 260, 262 to a desired position and then the respective clamp member 260, 262 can be released. Once released, springs 278 can urge clamp members 260, 262 from the second position 280 to the first position 272 where the clamp members impinge on support rods 274 so as to maintain the rods in the new or desired axially fixed position. It should be appreciated that while the above discussion of the quick-release clamp system 250 generally described clamp members 260, 262 being simultaneously moved from the first to second positions, each of the clamp members 260, 262 are separate components that can be used to individually or simultaneously adjust and lock a position of a corresponding support rod 274. Such individual adjustment of each support rod 274 can be used, for example, to align support pad 254 flush against claw plate 14, which can be at various angular orientations relative to the anatomy and longitudinal axis B.

Figure 11:
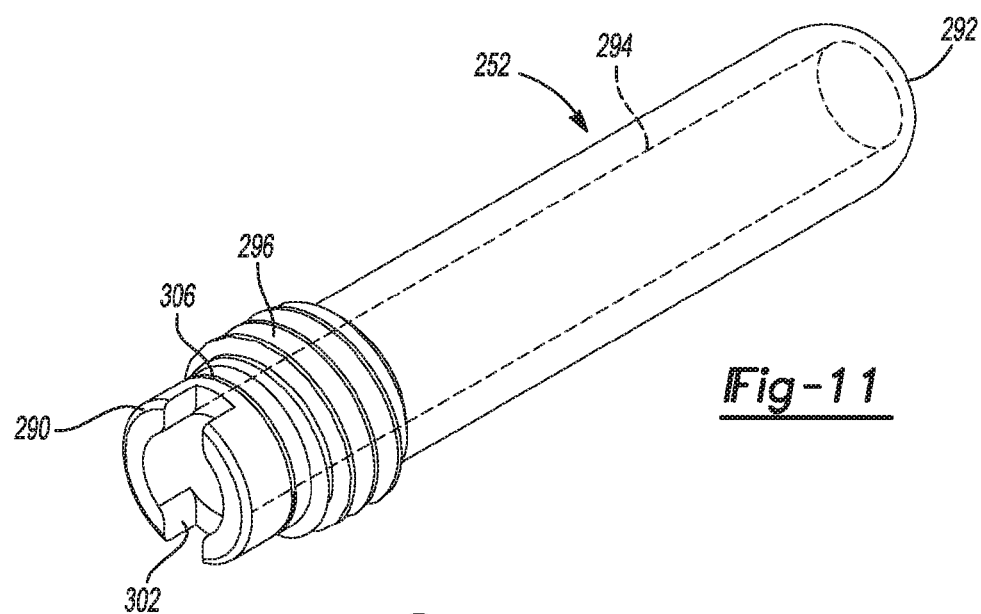
FIG. 11 is perspective view of a removable sleeve of the guide assembly of FIG. 10 according to the present teachings.

With particular reference to FIGS. 10-11, the removable sleeve 252 can include a first end 290, a second end 292 and an internal longitudinal bore 294 extending through sleeve 252. The removable sleeve 252 can be received in alignment tube 238 so as to be coaxial therewith and can include an external threaded portion 296 configured to threadingly engage an internal threaded portion 300 of alignment tube 238, as generally shown in FIGS. 10 and 11. First end 290 of removable sleeve 252 can also include an engagement or drive portion, such as slot 302, configured to receive a driving tool (not shown) to advance or retract threaded sleeve 252 relative to alignment tube 238. The removable sleeve 252 can be advanced relative to alignment tube 238 to have second end 292 engage the claw plate 14 against the soft tissue before the trochanteric bolt 60 is implanted. The removable sleeve 252 can further include a suitable marking, such as scribe line 306, that can be visible through a window 308 in alignment tube 238. The alignment tube 238 can also include a measurement index or indicia, such as a plurality of trochanteric bolt 60 or fastener length designations 310, positioned adjacent the window 308 such that scribe line 306 can be correlated to one of the length designations 310, as will be described in greater detail below.

The removable sleeve 252 can receive a trephine or drill 316 in longitudinal bore 294 so as to align and guide drill 316 (FIG. 17) in forming lateral bore 72. Drill 316 can include a stop member, such as an annular collar 318, positioned on a body 320 of drill 316 configured to abut a first end 324 of alignment tube 238 when drill 316 is inserted into alignment tube 238 and removable sleeve 252, as will be described in greater detail below. The collar 318 can be positioned relative to a tip 328 of drill 316 such that a desired drill depth is achieved when collar 318 abuts alignment tube 238 during a procedure. It should be appreciated that drill 316 can include a plurality of drills 316 each with collar 318 positioned at various distances relative to tip 328 to correspond with different desired drill depths, as may be required, for example, by different size femoral implants 12 and/or the use of lateral augments 102, 104.

Figure 18:
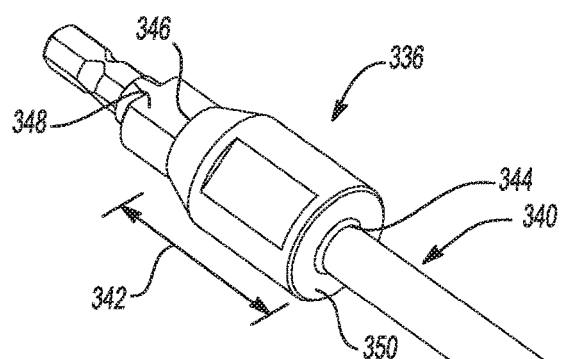

In an alternative configuration, and with additional reference to FIG. 18, a spacer sleeve 336 can be used as an alternative to the above described drill stop member arrangement. More specifically, as an alternative to using various drills 316 each with a differently positioned collar 318 corresponding at least to different implant configurations, one drill 340 can be used along with a plurality of different spacer sleeves 336, where each spacer sleeve 336 has a length 342 corresponding to a desired drill depth for the various implant configurations. Spacer sleeve 336 can include a longitudinal bore 344 configured to receive drill 340, a first end 346 arranged to abut portion 348 of drill 340, and a second end 350 configured to abut alignment tube 238 to serve as a stop to limit the drill depth to the predetermined amount that corresponds to the selected spacer sleeve 336.

Figure 12:
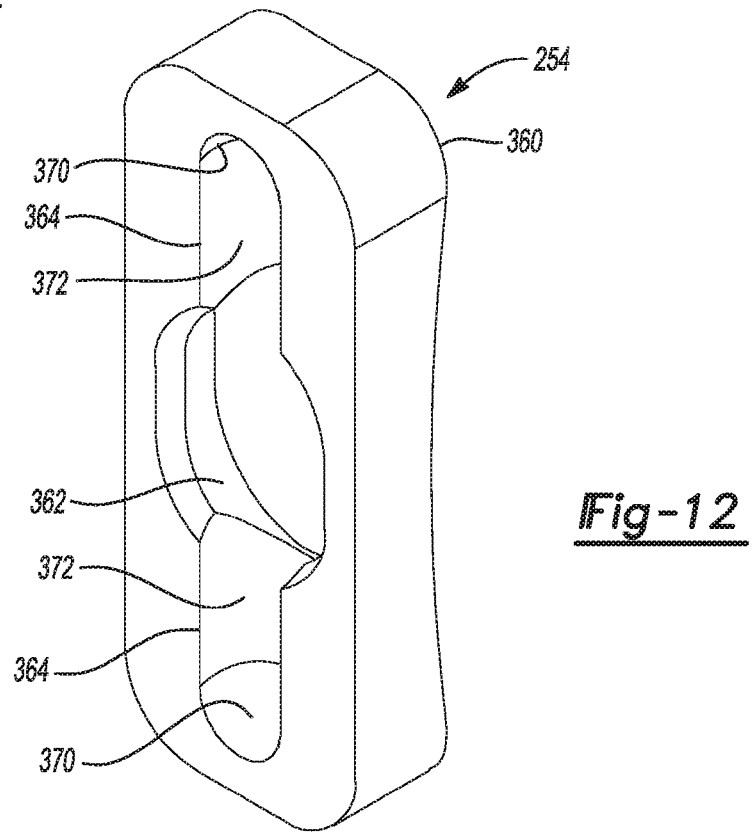
FIG. 12 is a perspective view of a support pad of the guide assembly of FIG. 10 according to the present teachings.

With particular reference to FIG. 12, and continued reference to FIGS. 10-14, the support pad 254 can include a generally rectangular shape 360, an aperture 362 for slidably receiving removable sleeve 252 therethrough, and retention slots 364. The support pad 254 can be removable received on circular or spherical engagement members 368 positioned on respective ends of support rods 274. The retention slots 364 can include a generally cylindrical shape 370 with an arcuate surface or periphery 372 that extends for greater than 180 degrees such that the slots 364 can capture the engagement members 368 and couple support pad 254 to support rods 274. As one of ordinary skill in the art will appreciate, the circular or spherical engagement members 368 provide for the ability to orientate the support pad 254 in various angular orientations relative to the support rods 274.

Referring to FIGS. 15-20B, and with continuing reference to FIGS. 1-3B, a procedure for inserting the claw plate 14, trochanteric bolt 60 and lateral augments 102 or 104, as may be required, will now be described. Although the procedure is illustrated with respect to the left-handed outrigger 210, it should be appreciated that the procedure is similarly applicable to the right-handed outrigger discussed above. It should also be appreciated that the bone and soft tissue are not illustrated in FIGS. 16-20B so as to not obscure the illustration of the guide assembly 200. Reference is made to FIGS. 1-3B and 15 for illustration of the bone and soft tissue.

Figure 15:
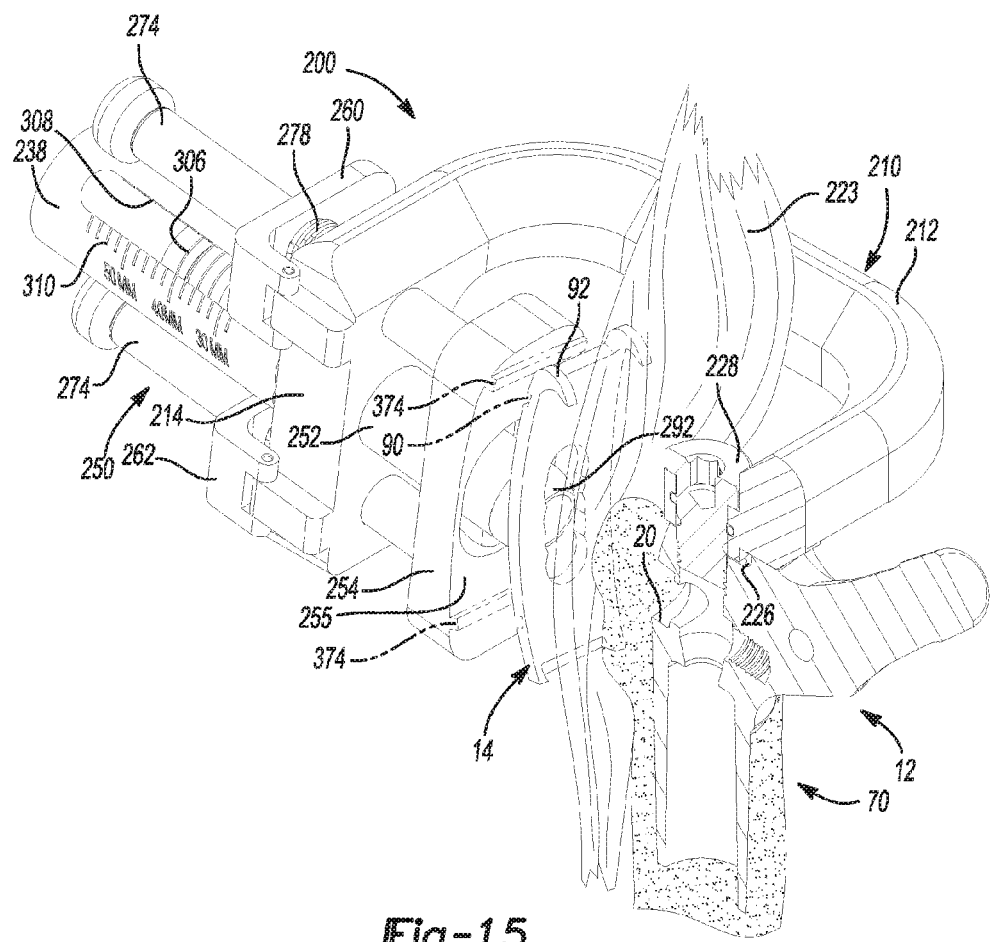
Figure 16:
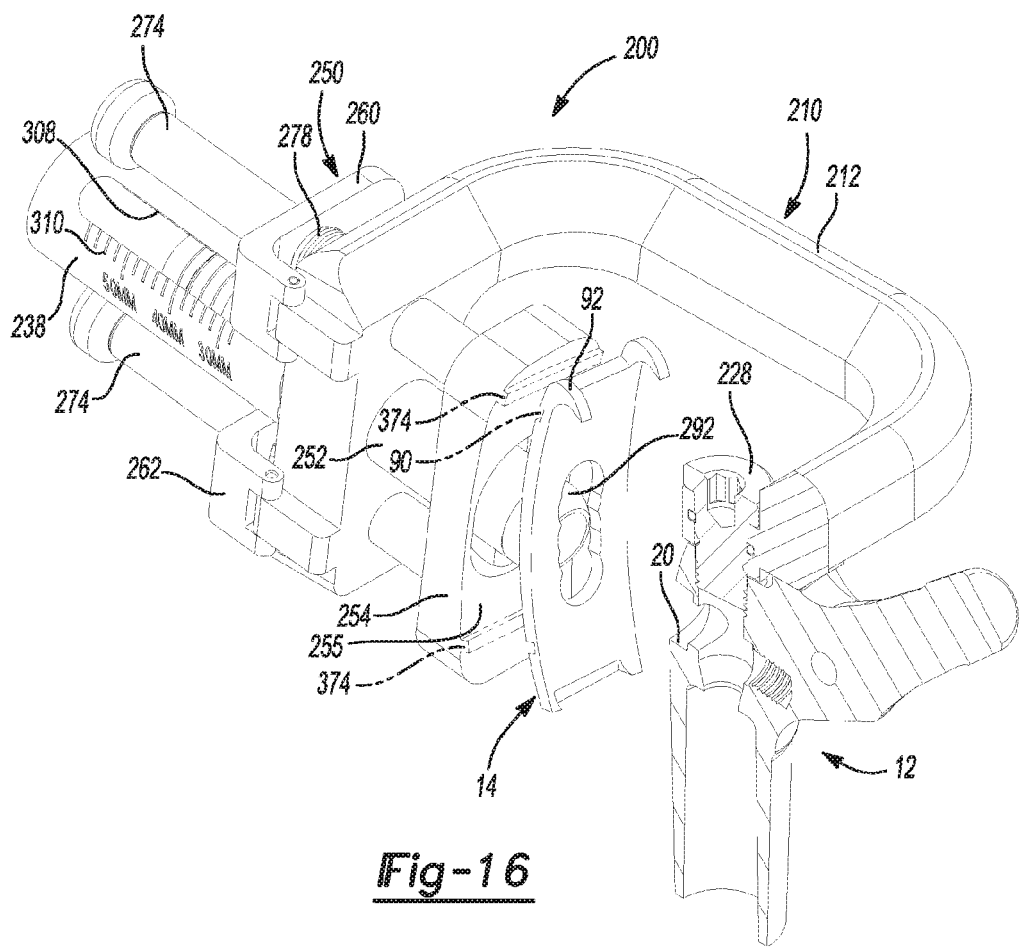
Figure 16A:
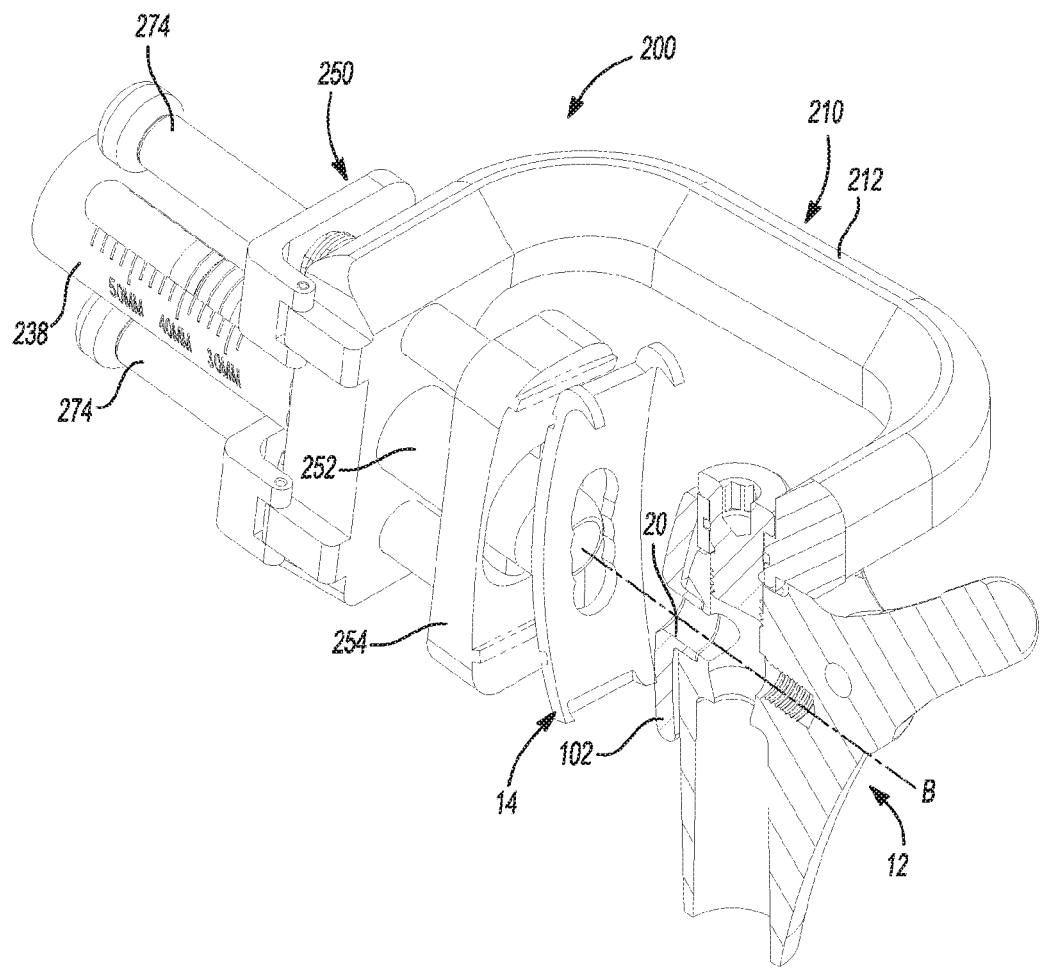

With the proximal femoral body 12 implanted, one of the lateral augments 102, 104 can be secured to the lateral side of femoral body 12, as may be required to provide proper positioning of the greater trochanter relative to proximal femoral body 12 and to account for the above noted bone loss. The outrigger 210 can be coupled to the proximal end 18 of proximal femoral body 12 and secured with fastener 228. Once coupled, alignment tube 238 can be coaxially aligned with blind bore 20, as shown in FIG. 15. The claw plate 14 can then be implanted and compressed against soft tissue 80 adjacent the femur 70 by advancing removable sleeve 252 such that second end 292 engages claw plate 14, as generally shown in FIGS. 16-17 with reference to FIGS. 1-3B. It should be appreciated that claw plate 14 can be adjusted superiorly or inferiorly relative to longitudinal axis B, as may be required based on various anatomical conditions. A suitable driver (not shown) can be coupled to the first end 290 of removable sleeve 252 so as to engage slot 302 and assist in advancing removable sleeve 252 to compress claw plate 14.

Once claw plate 14 is compressed with removable sleeve 252, clamp members 260, 262 can be independently depressed to release support rods 274. Support rods 274 can then be individually or simultaneously translated forward to engage support pad 254 with claw plate 14, as shown in FIGS. 16-17. Support pad 254 includes a smooth engagement surface 255 for engaging claw plate 14; however, support pad 254 can alternatively include projections 374 that engage slots 90 in claw plate 14, as also shown in FIG. 17. Once support pad 254 is engaged with claw plate 14, clamp members 260, 262 can be released thereby maintaining the position and support rods 274 and thus support pad 254.

With additional reference to FIGS. 17-18, the appropriately sized drill 316 corresponding to the implanted femoral body 12 and lateral augment 102, 104, if used, can be inserted into longitudinal bore 294 of removable sleeve 252 to drill the lateral bore 72 into the femur 70 from the lateral side 68. The drill 316 can be advanced until collar 318 engages alignment tube 238, as shown in FIG. 17. Alternatively, drill 340 could be used with an appropriately selected spacer sleeve 336 to form the lateral bore 72.

Once bore 72 is formed, drill 316 or 340 can be removed from sleeve 252 and an appropriate trochanteric bolt length can be determined by correlating the scribe line 306 with the length designations 310 on alignment tube 238. The length designation 310 aligned with scribe line 306 can correspond to the appropriate trochanteric bolt 60 length required to secure claw plate 14 to blind bore 20 while taking into account the thickness of bone and/or soft tissue being compressed by claw plate 14. It should be noted that the appropriate fastener length can also be determined before bore 72 is formed, such as after claw plate 14 is compressed by advancing removable sleeve 252.

Figure 19:
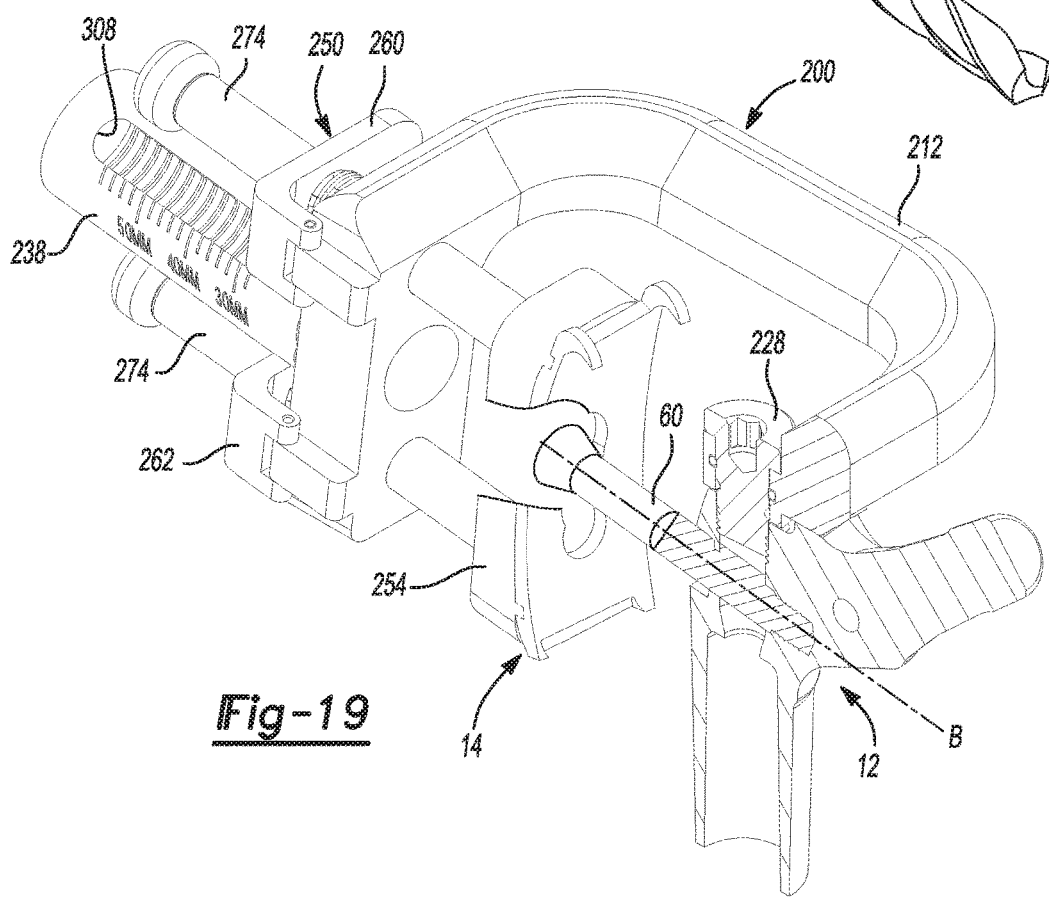
Figure 20:
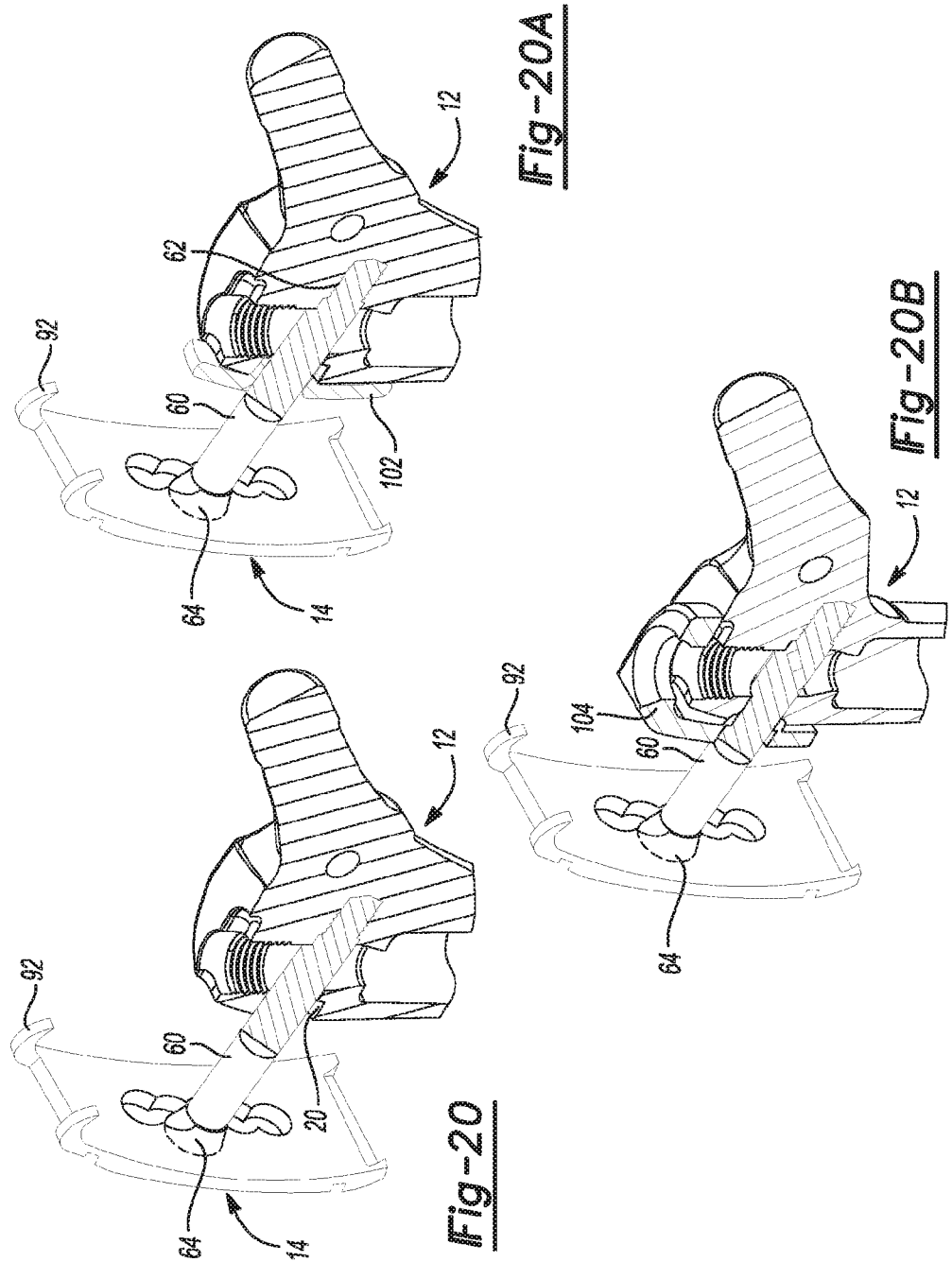

With the appropriate trochanteric bolt length determined by selecting a bolt length corresponding to the length designation 310 aligned with scribe line 306, sleeve 252 can be removed from alignment tube 238 while support pad 254 continues to compress claw plate 14 in place via support rods 274, as generally shown in FIG. 19. The selected trochanteric bolt 60 can then be implanted by passing bolt 60 through alignment tube 238 and aperture 362 of support pad 254 such that threaded end 62 engages threaded portion 26 of blind bore 20. Trochanteric bolt 60 can then be tightened such that head 64 engages and secures claw plate 14, as generally shown in FIGS. 20-20B with reference to FIG. 2-3B. Once the trochanteric bolt 60 is implanted and secured, the guide assembly 200 can be removed from proximal femoral body 12.

Figure 21:
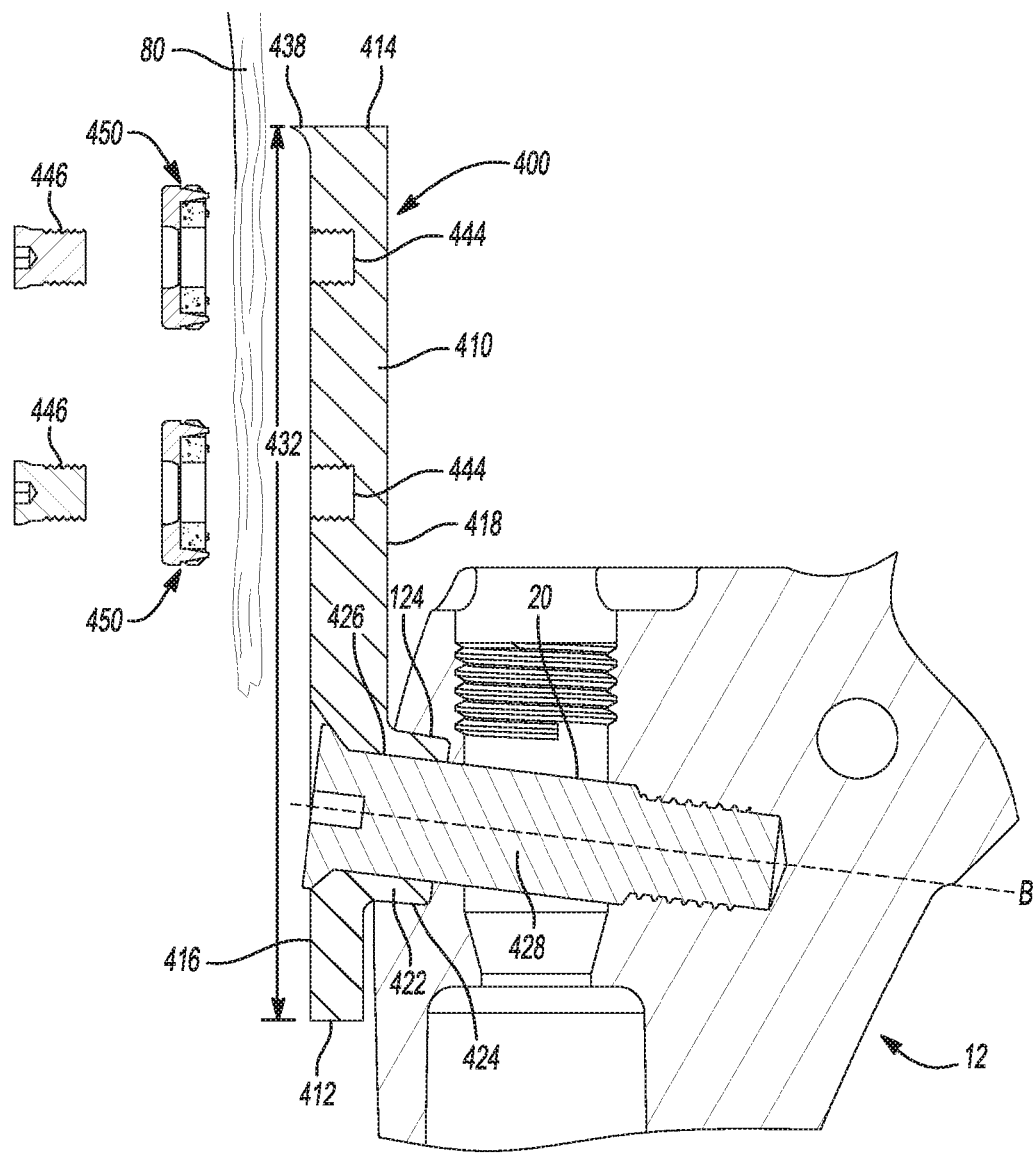
FIG. 21 is a sectional view of an alternative implant assembly according to the present teachings.

With additional reference to FIGS. 21-25, an alternative lateral implant 400 for attaching the soft tissue 80 to proximal femoral body 12 will now be described. Lateral implant 400 can include a generally T-shaped plate member 410 having a proximal end 412, a distal end 414, a lateral surface 416 and a medial surface 418 opposite lateral surface 416. The plate member 410 can include a tapered projection 422 extending from medial surface 418 and configured to be received in tapered counterbore 124 of proximal femoral body 12 and coupled thereto via a Morse taper connection 424. An aperture 426 can be provided in plate member 410 extending through projection 422 so as to be coaxial with blind bore 20 when the tapered projection 422 is received in counterbore 124, as generally shown in FIG. 21. A fastener 428 can be received through aperture 426 and threadingly engaged to bore 20 to secure plate member 410 to proximal femoral body 12, as generally shown for example in FIG. 21.

Plate member 410 can be configured to have a length 432 such that proximal end 414 extends sufficiently beyond proximal end 18 of femoral body 12 so as to provide for adequate soft tissue 80 attachment and support. Plate member 410 can also include a layer of porous metal coating, or can alternatively be formed entirely of porous metal. A pair of threaded blind bores 444 can be provided in plate member 410 extending from front surface 416. Bores 444 can be configured to receive a corresponding pair of fasteners 446 for securing soft tissue 80 to a lateral side of plate member 410, as generally shown in FIG. 21. Proximal end 414 can also include an attachment member, such as a sharp projection or tooth 438, to assist in attaching and retaining soft tissue 80.

Figure 24:
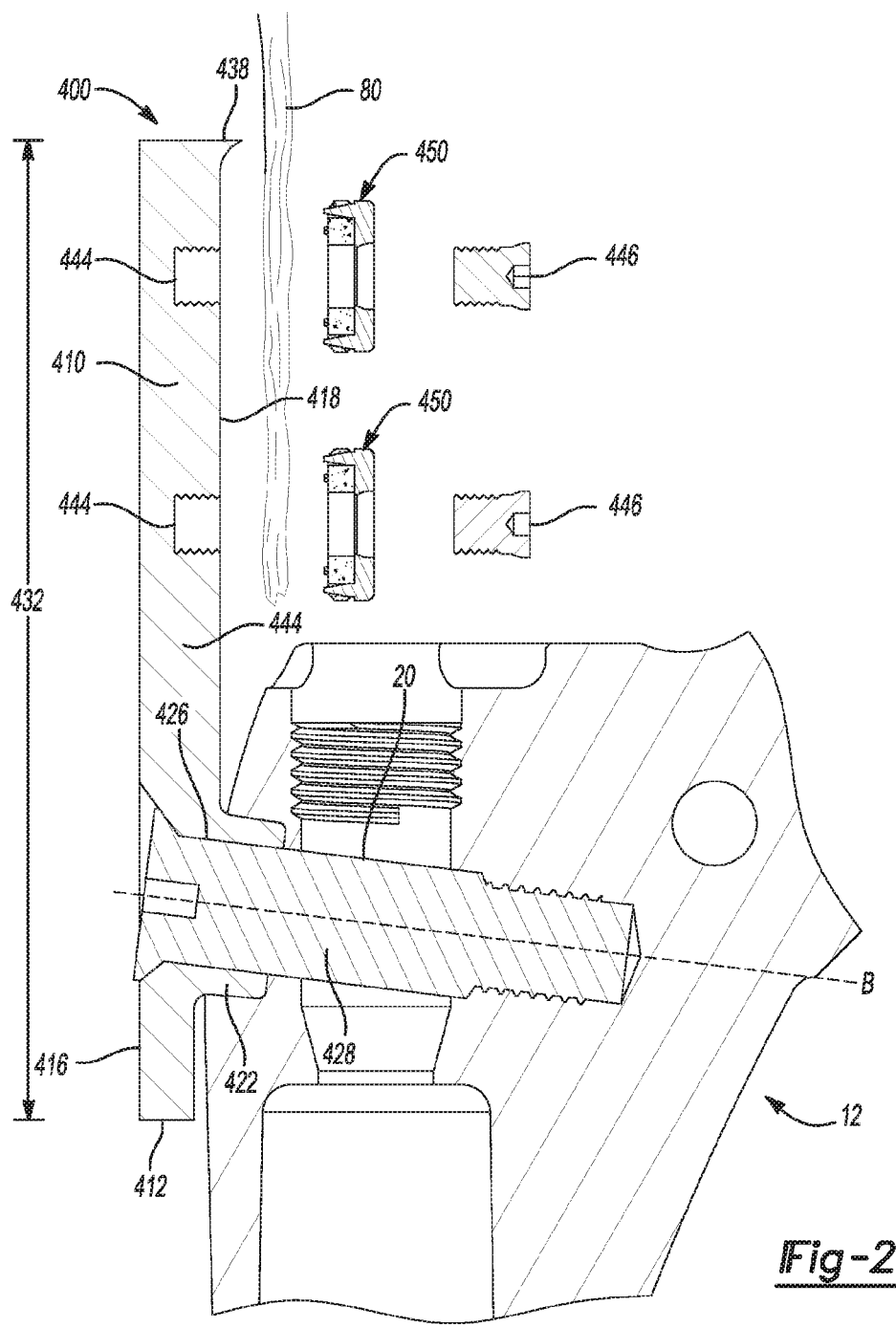
FIG. 24 is a sectional view of an alternative configuration of the implant assembly of FIG. 21 according to the present teachings.
Figure 25:
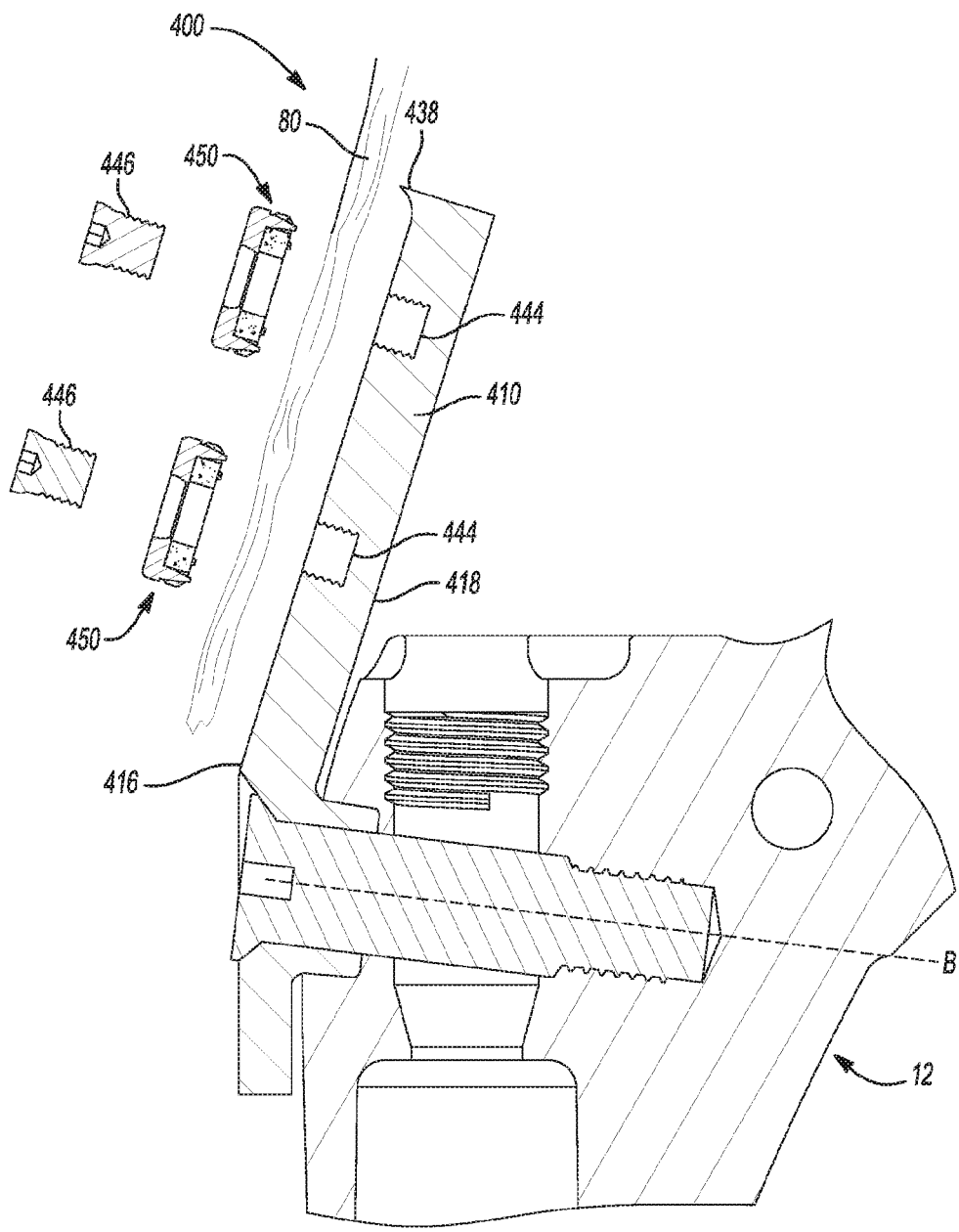
FIG. 25 is a sectional view of another alternative configuration of the implant assembly of FIG. 21 according to the present teachings.

In an alternative configuration, plate member 410 can include blind bores 444 extending from the medial surface 418, as generally shown in FIG. 24. In this configuration, the soft tissue 80 would be compressed against the medial surface of plate member 410, as also shown in FIG. 24. In another alternative configuration, plate member 410 can be angled so as to align with a force generated by the soft tissue, as generally shown in FIG. 25.

Figure 22:
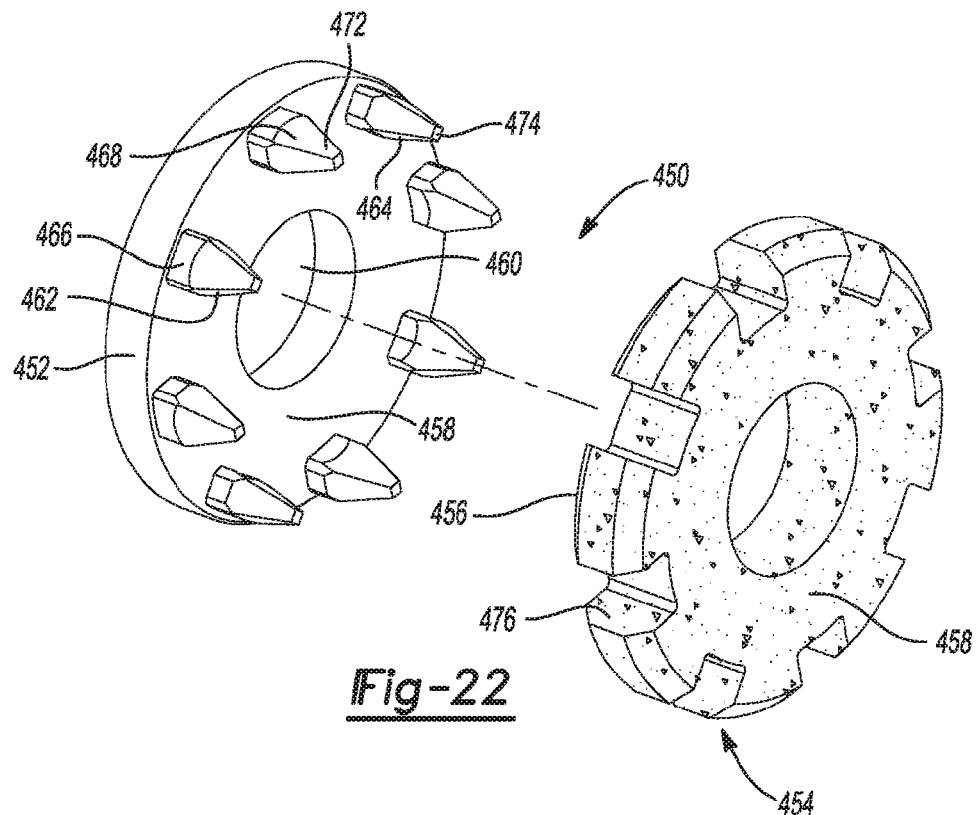
FIG. 22 is an exploded perspective view of a ligament washer of implant assembly of FIG. 21 according to the present teachings.
Figure 23:
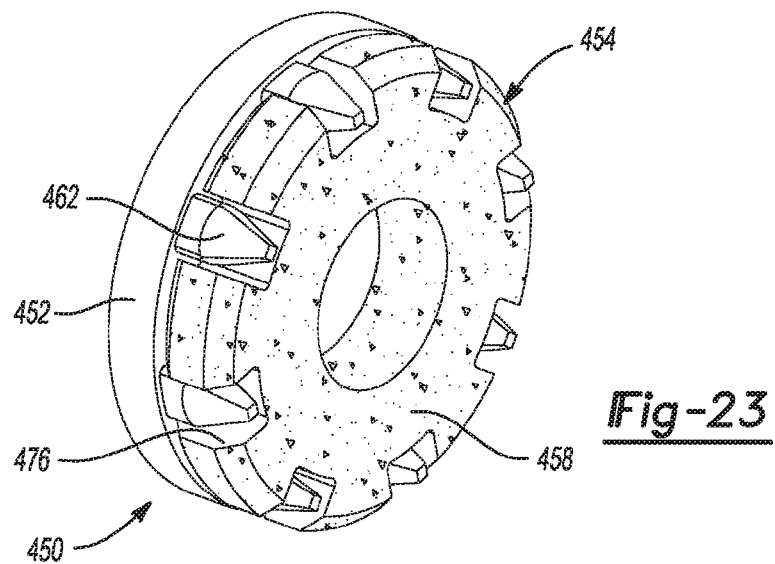
FIG. 23 is a perspective view of an exemplary assembled configuration of the ligament washer of FIG. 22 according to the present teachings.

Lateral implant 400 can also include ligament washers 450 for use with fasteners 446. Each ligament washer 450 can include a body portion 452 and an optional insert 454 configured to abut body portion 452, as shown in FIGS. 22-23 and generally described in commonly owned co-pending application Ser. No. 12/398,548, entitled "Method and Apparatus for Attaching Soft Tissue to an Implant," the entirety of which is hereby incorporated by reference herein. Body portion 452 can include a fastener engaging side 456, a soft tissue facing side 458, an aperture 460 and a plurality of circumferentially spaced ligament engagement members 462. The soft tissue facing side 458 can be configured to engage the soft tissue 80 directly or receive insert 454. Insert 454 can be configured to facilitate biologic fixation and can be coated with a layer of Regenerex® for such purpose. Alternatively, insert 454 can be formed entirely of porous metal. The plurality of bone engagement members 462 can each include a tapered configuration 464 formed with a base portion 466 attached to the soft tissue facing side 458 and a body portion 468 with multi-faceted side portions 472 that taper to a pointed distal tip 474. Insert 454 can further include a plurality of peripheral cut-outs or recesses 476 corresponding to the plurality of engagement members 462 such that each engagement member 462 is received in a recess 476, as generally shown in FIGS. 22-23. In use, the ligament washers can be received on fasteners 446 such that the insert 454 and engagement members 462 contact the soft tissue when the fasteners are secured to plate member 410, as shown in FIGS. 21 and 24-25.

While one or more specific examples have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

What is claimed is:

1. A femoral implant for a hip, comprising:
   a proximal femoral body implant comprising:
      a proximal femoral body portion;
      a distal stem coupled to the proximal femoral body portion; and
      a femoral head coupled to a neck portion of the proximal femoral body portion;
   a lateral plate having a T-shaped configuration coupled to a lateral side of the proximal femoral body implant, the lateral plate comprising:
      a lateral surface and a medial surface configured to be positioned adjacent to at least the lateral side of the proximal femoral body implant, at least one of the medial and lateral surfaces of the lateral plate defining a soft tissue attachment surface;
      a projection extending from the medial surface and being configured to mate with a recess formed in the lateral side of the proximal femoral body implant;
      an aperture formed in the lateral plate and extending through the projection such that the aperture is configured to be coaxially aligned with a lateral bore formed in the proximal femoral body implant; and
      at least one threaded bore extending from one of the lateral surface or the medial surface, the threaded bore being configured to receive a plate fastener for securing soft tissue to the lateral plate; and
   an implant fastener configured to be received through the aperture and configured to be threadably secured to the lateral bore of the proximal femoral body implant to couple the lateral plate to the proximal femoral body implant, the fastener having a length sufficient to also pass through a portion of the femur for securing the portion of the femur to the lateral plate and the proximal femoral body implant,
   wherein the recess is coaxial with the lateral bore formed in the proximal femoral body implant,
   wherein the projection includes a tapered cylindrical portion and the recess includes a complementary shaped tapered counterbore adapted to receive the tapered cylindrical portion in a press fit configuration, and
   wherein the lateral plate further comprises a proximal end adapted to extend a distance beyond a proximal end of the proximal femoral body implant, the proximal end of the lateral plate including a sharp projection configured to attach the lateral plate to the soft tissue.

2. The implant of claim 1, wherein the at least one threaded bore includes at least two threaded bores, wherein each of the at least two threaded bores extend from the other of the lateral surface and the medial surface.

3. The implant of claim 1, wherein the lateral plate is configured to be angled to align with a force generated by the soft tissue.

4. The implant of claim 1, wherein the proximal end of the lateral plate includes an attachment member configured to attach the lateral plate to the soft tissue.

5. The implant of claim 4, wherein the attachment member includes the lateral surface of the lateral plate.

6. The implant of claim 4, wherein the attachment member includes the medial surface of the lateral plate.

7. The implant of claim 1, wherein the lateral plate includes a layer of porous metal to enhance biologic fixation.

8. A femoral implant for a hip, comprising:
   a proximal femoral body implant comprising:
      a proximal femoral body portion;
      a distal stem coupled to the proximal femoral body portion; and
      a femoral head coupled to a neck portion of the proximal femoral body portion;
   a plate fastener;
   a lateral plate having a T-shaped configuration coupled to a lateral side of the proximal femoral body implant, the lateral plate comprising:
      a lateral surface and a medial surface configured to be positioned adjacent to at least the lateral side of the proximal femoral body implant, at least one of the medial and lateral surfaces of the lateral plate defining a soft tissue attachment surface;
      a projection extending from the medial surface and being configured to mate with a recess formed in the lateral side of the proximal femoral body implant;
      an aperture formed in the lateral plate and extending through the projection such that the aperture is configured to be coaxially aligned with a lateral bore formed in the proximal femoral body implant; and
      at least one threaded bore extending from one of the lateral surface or the medial surface, the threaded bore being configured to receive the plate fastener for securing soft tissue to the lateral plate; and
   an implant fastener configured to be received through the aperture and configured to be threadably secured to the lateral bore of the proximal femoral body implant to couple the lateral plate to the proximal femoral body implant, the fastener having a length sufficient to also pass through a portion of the femur for securing the portion of the femur to the lateral plate and the proximal femoral body implant,
   wherein the recess is coaxial with the lateral bore formed in the proximal femoral body implant,
   wherein the projection includes a tapered cylindrical portion and the recess includes a complementary shaped tapered counterbore adapted to receive the tapered cylindrical portion in a press fit configuration, and
   wherein the lateral plate further comprises a proximal end adapted to extend a distance beyond a proximal end of the proximal femoral body implant, the proximal end of the lateral plate including a sharp projection configured to attach the lateral plate to the soft tissue.

9. The implant of claim 8, wherein the lateral plate includes a layer of porous metal to enhance biologic fixation.

10. The implant of claim 8, further comprising a ligament washer including an aperture configured to receive the plate fastener.

11. The implant of claim 10, wherein the ligament washer comprises a body portion including a fastener engaging side and a soft tissue facing side, the soft tissue facing side including a plurality of circumferentially spaced ligament engagement members.

12. The implant of claim 11, wherein the ligament washer further comprises an insert configured to abut the body portion of the ligament washer.

13. The implant of claim 12, wherein the insert is coated with a layer of porous material.

14. The implant of claim 12, wherein the insert is formed entirely of porous metal.

\* \* \* \* \*